(12) United States Patent
Bourrie et al.

(10) Patent No.: US 7,812,165 B2
(45) Date of Patent: Oct. 12, 2010

(54) 6-SUBSTITUTED PYRIDOINDOLONE DERIVATIVES, PRODUCTION AND THERAPEUTIC USE THEREOF

(75) Inventors: Bernard Bourrie, Saint-Gély-du-Fesc (FR); Pierre Casellas, Montpellier (FR); Paola Ciapetti, Altorf (FR); Jean-Marie Deroco, Murviel-les-Montpellier (FR); Samir Jegham, Montferrier-sur-Lez (FR); Yvette Muneaux, Les Matelles (FR); Camille-Georges Wermuth, Strasbourg (FR)

(73) Assignee: sanofi-aventis, Paris (FR)

( * ) Notice: Subject to any disclaimer, the term of this patent is extended or adjusted under 35 U.S.C. 154(b) by 1002 days.

(21) Appl. No.: 11/582,769

(22) Filed: Oct. 18, 2006

(65) Prior Publication Data
US 2007/0129365 A1    Jun. 7, 2007

Related U.S. Application Data

(63) Continuation of application No. PCT/FR2005/000971, filed on Apr. 20, 2005.

(30) Foreign Application Priority Data
Apr. 21, 2004   (FR) ................................. 04 04251

(51) Int. Cl.
C07D 571/02 (2006.01)
A61K 31/4745 (2006.01)

(52) U.S. Cl. ......................................... 546/80; 514/290

(58) Field of Classification Search ................... 546/80; 514/290
See application file for complete search history.

(56) References Cited

U.S. PATENT DOCUMENTS

| | | | |
|---|---|---|---|
| 4,263,304 A | 4/1981 | Ishizumi et al. | |
| 4,835,160 A | 5/1989 | Bisagni et al. | |
| 5,880,126 A | 3/1999 | Skuballa et al. | |
| 6,503,888 B1 | 1/2003 | Kaplitt et al. | |
| 6,967,203 B2 | 11/2005 | Bourrie et al. | |
| 2002/0156016 A1 | 10/2002 | Minuk | |
| 2004/0122036 A1 | 6/2004 | Bourrie et al. | |
| 2005/0222192 A1 | 10/2005 | Bourrie et al. | |
| 2005/0288318 A1 | 12/2005 | Bourrie et al. | |
| 2008/0262020 A1* | 10/2008 | Muneaux et al. | 514/292 |

FOREIGN PATENT DOCUMENTS

| FR | 2 003 999 | 11/1969 |
|---|---|---|
| FR | 2 765 581 | 1/1999 |
| FR | 2 765 582 | 1/1999 |
| GB | 1 268 772 | 3/1972 |
| SU | 833971 | 5/1981 |
| WO | WO 99/51597 | 10/1999 |
| WO | WO 01/09129 | 2/2001 |
| WO | WO 02/087574 | 11/2002 |
| WO | WO 02/087575 | 11/2002 |
| WO | WO 2004/037821 | 5/2004 |
| WO | WO 2004/041817 | 5/2004 |
| WO | WO 2007/045758 | 4/2007 |

OTHER PUBLICATIONS

Estenne et al, Derwent Patent Abstract No. 199909 (2003), (Abstract of FR2 765 582).
Furihata, C., et al., In Vivo Short-Term Assays for Tumor Initiation and Promotion in the Grandular Stomach of Fischer Rats, Mutation Research, (1995), vol. 339, No. 1, pp. 15-35.
Furihata, C., et al., Unscheduled DNA Synthesis in Rat Stomach-Short-Term Assay of Potential Stomach Carcinogens, Banbury Report, (1982), vol. 13, pp. 123-135.
Goldman M.D., et al., Cecil, Textbook of Medicine, 21st station, vol. 1, published 2000 by W.B. Saunders Co. (PA), pp. 1060-1074.
Golovko, T., et al., A New Approach to the Synthesis of Functionally-Substituted Pyrido 2, 3-D Indoles, Mendeleev Communications, (1995), vol. 8, pp. 226-227.
Molina, P., et al., Annulation of Pyridine to Indole by a Tandem Aza-Wittig/Electrocyclization Strategy: Synthesis of Pyrido 2, 3-B Indoles, Synthesis, (1989), vol. 11, pp. 878-880.
Abstract No. 1982-25808E (XP-002184731, DW 198213) (1982).
Goodman & Gilman, Section X. Chemotherapy of Neoplastic Diseases, Goodman & Gilman's the Pharmacological Basis of Therapeutics, 9th Ed., (1996) pp. 1225-1232 and pp. 1269-1271.
Nicholson-Guthrie et al, Urine GABA Levels in Ovarian Cancer Patients: elevated GABA in malignancy, Cancer Letters, vol. 162, Issue 1, (2001), pp. 27-30.

* cited by examiner

*Primary Examiner*—Rita J Desai
(74) *Attorney, Agent, or Firm*—Kelly L. Bender; R. Brian McCaslin

(57) ABSTRACT

Compounds of formula:

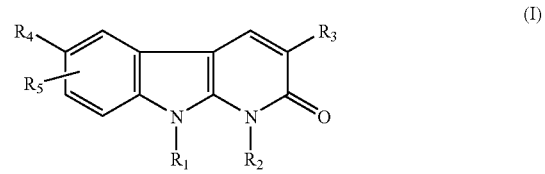

(I)

and pharmaceutically acceptable salts, hydrates, and solvates thereof, wherein $R_1$, $R_2$, $R_3$, $R_4$, and $R_5$, have the meanings given in the description; pharmaceutical compositions comprising said compounds; and processes for preparing said compounds and methods of use thereof.

9 Claims, No Drawings

6-SUBSTITUTED PYRIDOINDOLONE DERIVATIVES, PRODUCTION AND THERAPEUTIC USE THEREOF

The present invention relates to 6-substituted pyridoindolone derivatives, to their preparation and to their application in therapeutics.

French Patent 97 08409 describes compounds of formula

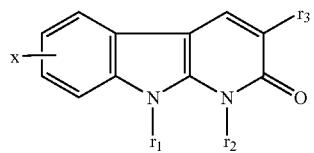

(A)

in which
- x represents a hydrogen or chlorine atom or a methyl or methoxy group;
- $r_1$ represents a hydrogen atom or a methyl or ethyl group;
- $r_2$ represents a methyl or ethyl group; or else
- $r_1$ and $r_2$ together form a $(CH_2)_3$ group; and
- $r_3$ represents either a phenyl group optionally substituted by a halogen atom or by a methyl or methoxy group, or a thienyl group.

In the description of that patent it is mentioned that the compounds of formula (A), having an affinity for the omega modulatory sites associated with $GABA_A$ receptors, can be used in the treatment of conditions related to the disorders of Gabaergic transmission associated with $GABA_A$ receptor subtypes, such as anxiety, sleep disorders, epilepsy, etc.

International patent applications WO 2002/087574 and WO 2002/087575 describe the use of compounds of formula (A) as anti-cancer agents and their combination with other anti-cancer agents.

International patent application WO 2004/041817 describes compounds of formula

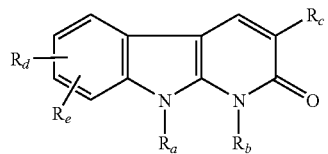

(B)

in which $R_a$, $R_b$, $R_c$, $R_d$ and $R_e$ have different values. These compounds exhibit an anti-cancer activity.

The present invention provides compounds conforming to the formula

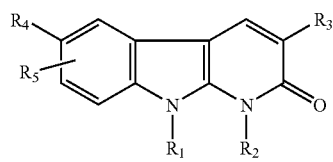

(I)

in which
- $R_1$ represents a hydrogen atom; a $(C_1\text{-}C_4)$alkyl group; a group $—(CH_2)_m OH$; a group $—(CH_2)_m CN$; or a group $—(CH_2)_m NR_9 R_{10}$;
- $R_2$ represents a hydrogen atom or a $(C_1\text{-}C_4)$alkyl group;
- $R_3$ represents a phenyl substituted by $R_6$, $R_7$, $R_8$;
- $R_4$ represents a group

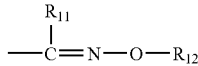

or
a heterocyclic radical selected from

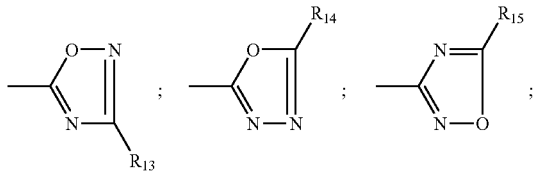

- $R_5$ represents a hydrogen atom or a $(C_1\text{-}C_4)$alkyl group;
- $R_6$, $R_7$ and $R_8$ represent, each independently of one another, a hydrogen atom; a halogen atom; a $(C_1\text{-}C_4)$alkyl group; a $(C_1\text{-}C_4)$alkoxy group; a hydroxyl; a cyano; a group $—(CH_2)_n NR_9 R_{10}$; or a group $—O—(CH_2)_m NR_9 R_{10}$;
- $R_9$ and $R_{10}$ represent, each independently of one another, a hydrogen atom or a $(C_1\text{-}C_4)$alkyl group;
- or else $R_9$ and $R_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a $(C_1\text{-}C_4)$ alkyl;
- $R_{11}$ represents a hydrogen atom or a $(C_1\text{-}C_4)$alkyl group;
- $R_{12}$ represents a hydrogen atom; a $(C_1\text{-}C_4)$alkyl group; or a group $—(CH_2)_m—CO—R_{16}$;
- $R_{13}$ represents a hydrogen atom; a $(C_1\text{-}C_4)$alkyl group; a phenyl; a group $—NR_{17}R_{18}$; or a

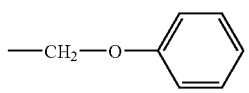

group;
- $R_{14}$ represents a hydrogen atom; a $(C_1\text{-}C_4)$alkyl group; or a group $—NR_{17}R_{18}$;
- $R_{15}$ represents a hydrogen atom; a $(C_1\text{-}C_4)$alkyl group; a group $—NR_{19}R_{20}$; or a $—COO(C_1\text{-}C_4)$alkyl group;
- $R_{16}$ represents a hydroxyl; a $(C_1\text{-}C_4)$alkoxy; or a group $—NR_9 R_{10}$;
- $R_{17}$ and $R_{18}$ represent, each independently, a hydrogen atom or a $(C_1\text{-}C_4)$alkyl group; $R_{18}$ may also represent a group $—COR_{21}$; or a group $—SO_2 R_{22}$;
- $R_{19}$ and $R_{20}$ represent, each independently, a hydrogen atom or a $(C_1\text{-}C_4)$alkyl group; $R_{20}$ may also represent a $(C_3\text{-}C_6)$cycloalkyl group, a $(C_3\text{-}C_6)$cycloalkylmethyl group or a group $—(CH_2)_m NR_9 R_{10}$;
- $R_{21}$ represents a $(C_1\text{-}C_4)$alkyl group; a $(C_3\text{-}C_6)$cycloalkyl group; or a group $—(CH_2)_m NR_9 R_{10}$;
- $R_{22}$ represents a $(C_1\text{-}C_4)$alkyl group;
- m is 1, 2 or 3; and
- n is 0, 1, 2 or 3.

The compounds of formula (I) may include one or more asymmetric carbon atoms. They may therefore exist in the form of enantiomers or diastereoisomers. These enantiomers and diastereoisomers and their mixtures, including the racemic mixtures, form part of the invention.

The compounds of formula (I) may exist in the form of bases or of addition salts with acids. Such addition salts form part of the invention.

These salts are advantageously prepared with pharmaceutically acceptable acids, although the salts of other acids which are of use, for example, for purifying or isolating the compounds of formula (I) also form part of the invention.

The compounds of formula (I) may also exist in the form of hydrates or solvates, namely in the form of combinations or associations with one or more molecules of water or with a solvent. Such hydrates and solvates also form part of the invention.

In the context of the present invention the terms are understood as follows:
- a halogen atom: a fluorine, a chlorine, a bromine or an iodine;
- a $(C_1-C_4)$alkyl group: a linear or branched saturated aliphatic group containing 1 to 4 carbon atoms. Examples include the groups methyl, ethyl, propyl, isopropyl, butyl, isobutyl and tert-butyl;
- a $(C_1-C_4)$ alkoxy group: an O-alkyl radical in which the alkyl group is as defined above.
- a $(C_3-C_6)$cycloalkyl group: a cyclic alkyl group of 3 to 6 carbon atoms such as the cyclopropyl, cyclobutyl, cyclopentyl or cyclohexyl group.

Among the compounds of formula (I) provided by the invention it is possible to mention the preferred compounds which are defined as follows:
$R_1$ represents a hydrogen atom or a $(C_1-C_4)$alkyl group;
$R_2$ represents a hydrogen atom or a $(C_1-C_4)$alkyl group;
$R_3$ represents a phenyl radical substituted by $R_6$, $R_7$, $R_8$;
$R_4$ represents a hydroxyimidoformyl or $(C_1-C_4)$alkoxyimidoformyl group or an oxadiazolyl radical unsubstituted or substituted by a $(C_1-C_4)$alkyl, phenyl or amino group;
$R_5$ represents hydrogen or a $(C_1-C_4)$alkyl group;
$R_6$, $R_7$ and $R_8$ represent, each independently of one another, a hydrogen or halogen atom or a $(C_1-C_4)$alkyl, $(C_1-C_4)$alkoxy, amino, monomethylamino or dimethylamino group.

Among the compounds of formula (I) provided by the invention it is also possible to mention the preferred compounds which are defined as follows:
$R_1$ represents a hydrogen atom, a methyl, an ethyl, a cyanomethyl or a 2-morpholin-4-ylethyl;
and/or $R_2$ represents a methyl;
and/or $R_3$ represents a phenyl, a 3-bromophenyl, a 4-bromophenyl, a 2-chlorophenyl, a 3-chlorophenyl, a 4-chlorophenyl, a 3-fluorophenyl, a 4-fluorophenyl, a 3-methylphenyl, a 2-methoxyphenyl, a 3-methoxyphenyl, a 4-methoxyphenyl, a 3-cyanophenyl, a 4-cyanophenyl, a 2,4-dichlorophenyl, a 3,5-difluorophenyl, a 2,4-dimethylphenyl, a 2,4-dimethoxyphenyl, a 2-methyl-5-fluorophenyl, a 3-fluoro-4-methylphenyl, a 3-methyl-4-fluorophenyl, a 4-(aminomethyl)phenyl, a 4-(morpholin-4-ylmethyl)phenyl or a 4-(2-morpholin-4-ylethoxy)phenyl;
and/or $R_4$ represents:
- a (hydroxyimino)methyl group, an N-hydroxyethanimidoyl group, an (ethoxyimino)methyl group, an N-ethoxyethanimidoyl group, an (isobutoxyimino) methyl group, a [(carboxymethoxy)imino]methyl group, a [(2-ethoxy-2-oxoethoxy)imino]methyl group or a [(2-morpholin-4-yl-2-oxoethoxy)imino] methyl group;
- a 3-methyl-1,2,4-oxadiazol-5-yl, a 3-phenyl-1,2,4-oxadiazol-5-yl, a 3-amino-1,2,4-oxadiazol-5-yl, a 3-(dimethylamino)-1,2,4-oxadiazol-5-yl, a 3-[(cyclopropylcarbonyl)amino]-1,2,4-oxadiazol-5-yl, a 3-[(N,N-dimethylglycyl)amino]-1,2,4-oxadiazol-5-yl, a 3[(methylsulphonyl)amino]-1,2,4-oxadiazol-5-yl or a 3-(phenoxymethyl)-1,2,4-oxadiazol-5-yl;
- a 5-methyl-1,3,4-oxadiazol-2-yl or a 5-amino-1,3,4-oxadiazol-2-yl; or
- a 5-methyl-1,2,4-oxadiazol-3-yl, a 5-amino-1,2,4-oxadiazol-3-yl, a 5-(dimethylamino)-1,2,4-oxadiazol-3-yl, a 5-(cyclopropylamino)-1,2,4-oxadiazol-3-yl, a 5-[(cyclopropylmethyl)amino]-1,2,4-oxadiazol-3-yl, a 5-[(3-morpholin-4-ylpropyl)amino]-1,2,4-oxadiazol-3-yl, a 5-[[2-(dimethylamino)ethyl]amino]-1,2,4-oxadiazol-3-yl or a 5-(ethoxycarbonyl)-1,2,4-oxadiazol-3-yl;

and/or $R_5$ represents a hydrogen atom; in the form of the base or addition salt with an acid, and in the hydrate or solvate form.

Among the compounds of this latter group it is possible to mention the compounds of formula (I) for which
$R_1$ represents a hydrogen atom, a methyl, an ethyl, a cyanomethyl or a 2-morpholin-4-ylethyl;
$R_2$ represents a methyl;
$R_3$ represents a phenyl, a 3-bromophenyl, a 4-bromophenyl, a 2-chlorophenyl, a 3-chlorophenyl, a 4-chlorophenyl, a 3-fluorophenyl, a 4-fluorophenyl, a 3-methylphenyl, a 2-methoxyphenyl, a 3-methoxyphenyl, a 4-methoxyphenyl, a 3-cyanophenyl, a 4-cyanophenyl, a 2,4-dichlorophenyl, a 3,5-difluorophenyl, a 2,4-dimethylphenyl, a 2,4-dimethoxyphenyl, a 2-methyl-5-fluorophenyl, a 3-fluoro-4-methylphenyl, a 3-methyl-4-fluorophenyl, a 4-(aminomethyl)phenyl, a 4-(morpholin-4-ylmethyl)phenyl or a 4-(2-morpholin-4-ylethoxy)phenyl;
$R_4$ represents:
- a (hydroxyimino)methyl group, an N-hydroxyethanimidoyl group, an (ethoxyimino)methyl group, an N-ethoxyethanimidoyl group, an (isobutoxyimino) methyl group, a [(carboxymethoxy)imino]methyl group, a [(2-ethoxy-2-oxoethoxy)imino]methyl group or a [(2-morpholin-4-yl-2-oxoethoxy)imino] methyl group;
- 3-methyl-1,2,4-oxadiazol-5-yl, a 3-phenyl-1,2,4-oxadiazol-5-yl, a 3-amino-1,2,4-oxadiazol-5-yl, a 3-(dimethylamino)-1,2,4-oxadiazol-5-yl, a 3-[(cyclopropylcarbonyl)amino]-1,2,4-oxadiazol-5-yl, a 3-[(N,N-dimethylglycyl)amino]-1,2,4-oxadiazol-5-yl, a 3[(methylsulphonyl)amino]-1,2,4-oxadiazol-5-yl or a 3-(phenoxymethyl)-1,2,4-oxadiazol-5-yl;
- a 5-methyl-1,3,4-oxadiazol-2-yl or a 5-amino-1,3,4-oxadiazol-2-yl; or
- a 5-methyl-1,2,4-oxadiazol-3-yl, a 5-amino-1,2,4-oxadiazol-3-yl, a 5-(dimethylamino)-1,2,4-oxadiazol-3-yl, a 5-(cyclopropylamino)-1,2,4-oxadiazol-3-yl, a 5-[(cyclopropylmethyl)amino]-1,2,4-oxadiazol-3-yl, a 5-[(3-morpholin-4-ylpropyl)amino]-1,2,4-oxadiazol-3-yl, a 5-[[2-(dimethylamino)ethyl]amino]-1,2,4-oxadiazol-3-yl or a 5-(ethoxycarbonyl)-1,2,4-oxadiazol-3-yl;

$R_5$ represents a hydrogen atom; in the form of the base or addition salt with an acid, and in the hydrate or solvate form.

Among the compounds of formula (I) provided by the invention it is possible in particular to mention the following compounds:

- 6-(3-amino-1,2,4-oxadiazol-5-yl)-3-(2,4-dichlorophenyl)-1,9-dimethyl-1,9-dihydro-2H-pyrido[2,3-b]indol-2-one;
- 3-(2,4-dichlorophenyl)-1,9-dimethyl-2-oxo-2,9-dihydro-1H-pyrido[2,3-b]indole-6-carbaldehyde oxime;
- 3-(2,4-dichlorophenyl)-1,9-dimethyl-2-oxo-2,9-dihydro-1H-pyrido[2,3-b]indole-6-carbaldehyde O-ethyloxime;
- 5-[3-(4-chlorophenyl)-1,9-dimethyl-2,9-dihydro-1H-pyrido[2,3-b]indol-6-yl]-1,2,4-oxadiazol-3-amine;
- 5-[3-(3-fluorophenyl)-1,9-dimethyl-2,9-dihydro-1H-pyrido[2,3-b]indol-6-yl]-1,2,4-oxadiazol-3-amine;
- 5-[1,9-dimethyl-3-(3-methylphenyl)-2,9-dihydro-1H-pyrido[2,3-b]indol-6-yl]-1,2,4-oxadiazol-3-amine;
- 3-[4-(aminomethyl)phenyl]-6-(3-amino-1,2,4-oxadiazol-5-yl)-1,9-dimethyl-1,9-dihydro-2H-pyrido[2,3-b]indol-2-one;
- 5-[1,9-dimethyl-3-[4-morpholin-4-ylmethyl)phenyl]-2,9-dihydro-1H-pyrido[2,3-b]indol-6-yl]-1,2,4-oxadiazol-3-amine;
- 5-[3-(2,4-dichlorophenyl)-1,9-dimethyl-2,9-dihydro-1H-pyrido[2,3-b]indol-6-yl]-1,3,4-oxadiazol-2-amine;
- N'-[3-[3-(2,4-dichlorophenyl)-1,9-dimethyl-2,9-dihydro-1H-pyrido[2,3-b]indol-6-yl]-1,2,4-oxadiazol-5-yl]-N,N-dimethylethane-1,2-diamine;

in the form of the base or addition salt with an acid, and in the hydrate or solvate form.

A protective group Gp or G'p below is a group which makes it possible on the one hand to protect a reactive function such as a hydroxyl or an amine during a synthesis and on the other hand to regenerate the reactive function intact at the end of synthesis. Examples of protective groups and also methods of protection and deprotection are given in "Protective Groups in Organic Synthesis", Green et al., 2nd Edition (John Wiley & Sons, Inc., New York, 1991).

A leaving group below is a group which is readily cleavable from a molecule by breakage of a heterolytic bond with the departure of an electron pair. This group may therefore be replaced readily by another group during a substitution reaction, for example. Leaving groups of this kind are, for example, halogens or an activated hydroxyl group such as a methanesulphonate, benzenesulphonate, p-toluenesulphonate, triflate, acetate, etc. Examples of leaving groups and also references for their preparation are given in "Advanced Organic Chemistry", J. March, 3rd Edition, Wiley Interscience, pp. 310-16, 1985.

In accordance with the invention the compounds of general formula (I) may be prepared according to the processes below.

In accordance with the invention the compounds of formula (I) in which $R_4$ represents a group $-CR_{11}=N-O-R_{12}$ may be prepared according to a process which is characterized in that a compound of the formula

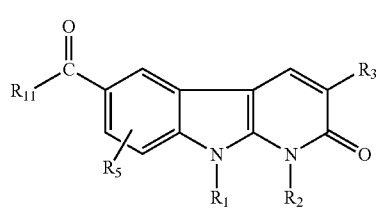

(II)

in which $R_1$, $R_2$, $R_3$, $R_5$ and $R_{11}$, are as defined for a compound of formula (I) is reacted with a hydroxylamine derivative of formula $$H_2N-O-R_{12} \quad (III)$$

in which $R_{12}$ is as defined for a compound of formula (I).

When $R_{11}=H$, the reaction takes place in a polar solvent such as an alcohol, for instance methanol or ethanol, at a temperature between the ambient temperature and the reflux temperature of the solvent.

When $R_{11}=(C_1-C_4)$alkyl, the reaction takes place in a polar solvent such as ethanol in the presence of a base such as an alkali metal carbonate, potassium carbonate for example, at a temperature between the ambient temperature and the reflux temperature of the solvent.

According to one variant of this process, with the proviso that $R_1$ and/or $R_2 \neq H$, a compound of formula (I) in which $R_4$ represents a group $-CR_{11}=N-O-R_{12}$ in which $R_{12}$ represents a $(C_1-C_4)$alkyl group or a group $-(CH_2)_m COR_{16}$ may be prepared by reacting a compound of formula (I) in which $R_4$ represents a group $-CR_{11}=N-OH$ with a halogenated derivative of formula Hal-$R_{12}$ in which Hal represents a halogen atom, preferably chlorine or bromine, in the presence of a base such as an alkali metal hydride, sodium hydride for example, in a solvent such as N,N-dimethylformamide and at a temperature between the ambient temperature and the reflux temperature of the solvent.

In accordance with the invention the compounds of formula (I) in which

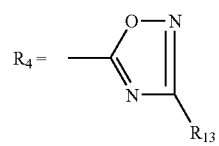

may be prepared according to a process which is characterized in that a compound of formula

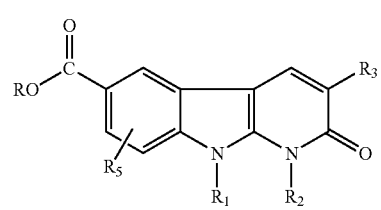

(IV)

in which $R_1$, $R_2$, $R_3$ and $R_5$ are as defined for a compound of formula (I) and R represents a hydrogen atom or a $(C_1-C_4)$ alkyl group is reacted with an oxime derivative of formula

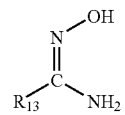

(V)

in which $R_{13}$ is as defined for a compound of formula (I).

When R in the compound of formula (IV) represents a hydrogen atom the reaction takes place in the presence of a coupling agent such as dicyclohexylcarbodiimide, carbonyldiimidazole, benzotriazol-1-yl-oxytris(dimethylamino)phosphonium hexafluorophosphate or benzotriazol-1-yloxytripyrrolidinophosphonium hexafluorophosphate, in a solvent such as dichloromethane or N,N-dimethylformamide and at a temperature between the ambient temperature and the reflux temperature of the solvent.

When R in the compound of formula (IV) represents a $(C_1$-$C_4)$alkyl group the reaction takes place in the presence of a base such as sodium hydride or sodium ethoxide in the presence of a desiccant such as zeolites, in a solvent such as dioxane, tetrahydrofuran or ethanol and at a temperature between the ambient temperature and the reflux temperature of the solvent.

According to one variant of this process, with the proviso that $R_1$ and/or $R_2 \neq H$, a compound of formula (I) in which

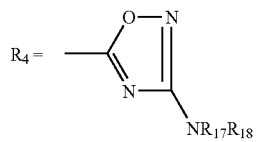

in which $R_{17}$ and/or $R_{18}$ represent a $(C_1$-$C_4)$alkyl may be prepared by reacting a compound of formula (I) in which

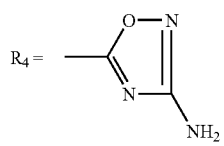

with a $(C_1$-$C_4)$alkyl halide in the presence of a base such as sodium hydride, in a solvent such as N,N-dimethylformamide and at a temperature between the ambient temperature and the reflux temperature of the solvent. Similarly, by reaction with a compound of formula $R_{21}COHal$ or $R_{22}SO_2Hal$ in which Hal represents a halogen atom, in the presence of a base such as pyridine or triethylamine, in a solvent such as dichloromethane or N,N-dimethylformamide, at a temperature between the ambient temperature and the reflux temperature of the solvent, the compounds of formula (I) are prepared in which

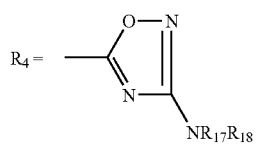

in which $R_{18}$=—$COR_{21}$ or —$SO_2R_{22}$.

In particular it is also possible to prepare a compound of formula (I) in which

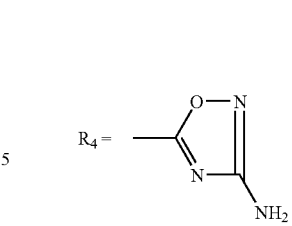

by following the various steps of the process described in Scheme I below.

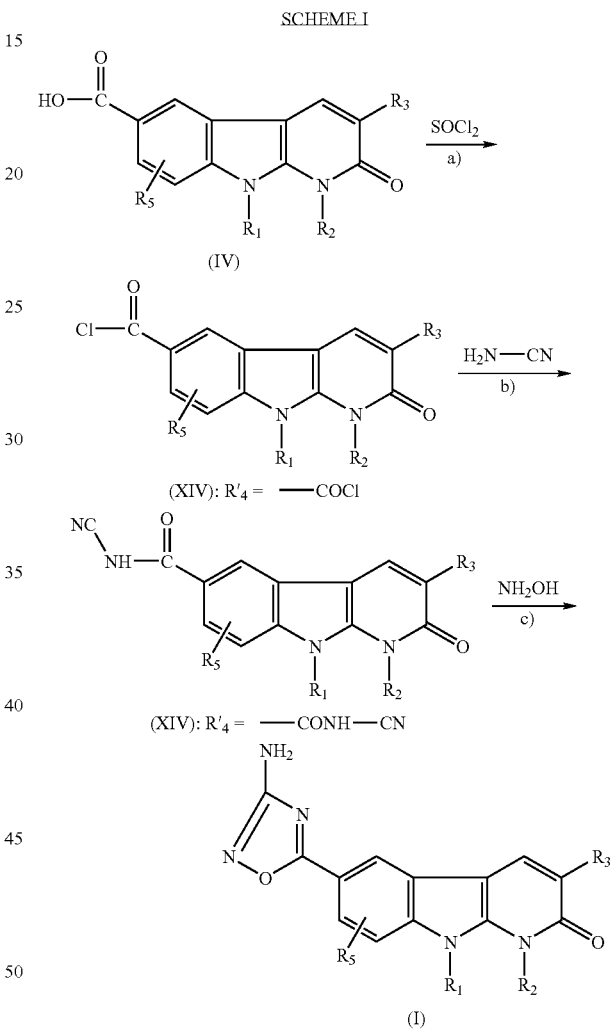

In step a) of Scheme I an acid of formula (IV) is reacted with thionyl chloride in a solvent such as tetrahydrofuran at a temperature between 0° C. and the ambient temperature to give the corresponding acid chloride.

In step b) the reaction of the acid chloride with cyanamide without solvent or in a solvent such as THF at a temperature between the ambient temperature and the reflux temperature of the solvent or the melting temperature of cyanamide makes it possible to obtain the corresponding N-cyanocarboxamide derivative, which, by reaction in step c) with hydroxylamine in a solvent such as pyridine, at a temperature between the ambient temperature and 120° C., makes it possible to obtain the expected compound of formula (I).

In accordance with the invention the compounds of formula (I) in which

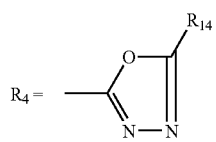

may be prepared according to a process which is characterized in that a compound of formula

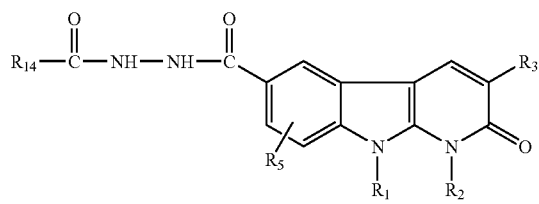

(IX)

in which $R_1$, $R_2$, $R_3$, $R_5$ and $R_{14}$ are as defined for a compound of formula (I) is cyclized.

The cyclization reaction takes place, generally, in the presence of a catalytic amount of an acid such as toluene-4-sulphonic acid, in a solvent such as toluene, at a temperature between the ambient temperature and the reflux temperature of the solvent, the water formed being removed azeotropically.

According to one variant of the process the cyclization is carried out by reacting the compound of formula (IX) with toluene-4-sulphonyl chloride in the presence of a base such as triethylamine, in a solvent such as dichloromethane and at a temperature between the ambient temperature and the reflux temperature of the solvent.

According to another variant of the process the cyclization is carried out in the presence of phosphorus oxychloride according to the process described in J. Org. Chem. USSR, 1989, 25 (5), 935-40.

In particular a compound of formula (I) in which

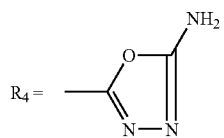

may be prepared by reacting a compound of formula

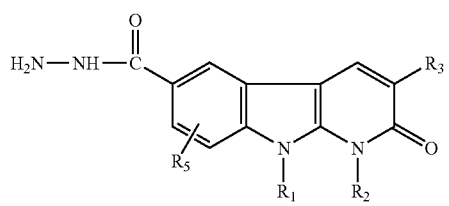

(X)

in which $R_1$, $R_2$, $R_3$ and $R_5$ are as defined for a compound of formula (I) with cyanogen bromide in a solvent such as methanol, at a temperature between the ambient temperature and the reflux temperature of the solvent, followed by a hydrolysis in basic medium.

In particular also, a compound of formula (I) in which

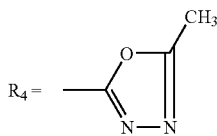

may be prepared by reacting a compound of formula (X) with triethyl orthoacetate, in the presence of a catalytic amount of an acid such as toluene-4-sulphonic acid, at a temperature between the ambient temperature and 150° C.

According to one variant of the process, with the proviso that $R_1$ and/or $R_2$=H, a compound of formula (I) in which

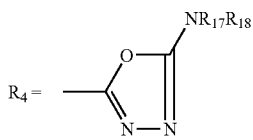

in which $R_{17}$ and/or $R_{18}$ represent a ($C_1$-$C_4$)alkyl, or $R_{18}$ may also represent —$COR_{21}$ or —$SO_2R_{22}$, may be prepared from a compound of formula (I) in which

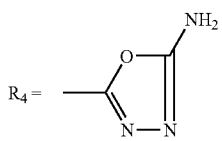

according to the methods described above.

In accordance with the invention the compounds of formula (I) in which

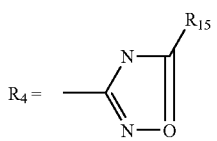

may be prepared according to a process which is characterized in that a compound of formula

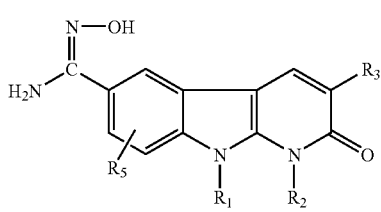

(XI)

in which $R_1$, $R_2$, $R_3$ and $R_5$ are as defined for a compound of formula (I) is reacted with a)—alternatively trichloroacetyl chloride, in the presence of a base, to give a compound of formula

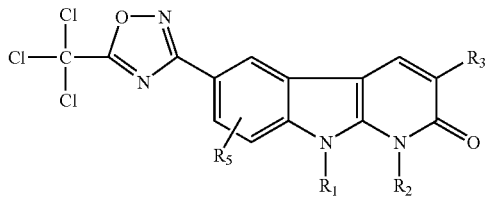

(XII)

and the compound of formula (XII) thus obtained is reacted with an amine of formula $HNR_{19}R_{20}$, when the preparation is required of a compound of formula (I) in which $R_{15}=NR_1R_{20}$;

b)—or an anhydride of formula $(R_{15}CO)_2O$, when the preparation is required of a compound of formula (I) in which $R_{15}=(C_1-C_4)$ alkyl;

c)—or a derivative of oxalic acid of formula

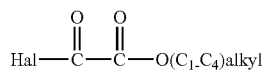

in which Hal represents a halogen atom, when the preparation is required of a compound of formula (I) in which $R_{15}=COO(C_1-C_4)$alkyl.

In step a), the reaction takes place in the presence of a base such as pyridine or N-methylpyrrolidin-2-one, in a solvent such as dioxane and at a temperature between the ambient temperature and the reflux temperature of the solvent. Then the reaction of the compound (XII) with the amine takes place in a solvent such as tetrahydrofuran or N,N-dimethyl-formamide and at a temperature between —78° C. and the ambient temperature.

In step b), the reaction takes place in the presence of an acid such as acetic acid at a temperature between the ambient temperature and the reflux temperature of the reaction mixture.

In step c), the reaction takes place in the presence of a base such as pyridine, in a solvent such as 1,2-dichloroethane and at a temperature between 0C and the reflux temperature of the solvent.

A compound of formula (I) in which $R_1$ and/or $R_2$ represent a $(C_1-C_4)$alkyl group may also be prepared by reacting a compound of formula (I) in which $R_1$ and/or $R_2$ represent a hydrogen atom with a $(C_1-C_4)$alkyl halide, in the presence of a base such as sodium hydride, in a solvent such as N,N-dimethylformamide and at a temperature between the ambient temperature and the reflux temperature of the solvent.

A compound of formula (I) in which $R_1$ represents a group —$(CH_2)_mOH$ may also be prepared by reacting a compound of formula (I) in which $R_1H$ with a compound of formula X—$(CH_2)_m$—O-Gp in which X is a leaving group as defined above and Gp is an O-protective group, in the presence of a base such as sodium hydride, in a solvent such as N,N-dimethylformamide and at a temperature between 0° C. and the reflux temperature of the solvent, and then treating the compound thus obtained to remove the O-protective group, according to known methods.

A compound of formula (I) in which $R_1$ represents a group —$(CH_2)_mCN$ may also be prepared by reacting a compound of formula (I) Hal-$(CH_2)_mCN$ in which Hal represents a halogen atom, in the presence of a base such as an alkali metal carbonate, for instance potassium carbonate, in a solvent such as N,N-dimethylformamide and at a temperature between the ambient temperature and the reflux temperature of the solvent.

A compound of formula (I) in which $R_1$ represents a group —$(CH_2)_mNR_9R_{10}$ may also be prepared by reacting a compound of formula (I) in which $R_1$=H with a compound of formula X-$(CH_2)_mNR_9R_{10}$ in which X represents a leaving group as defined above, in the presence of a base such as an alkali metal carbonate, for instance potassium carbonate, in a solvent such as N,N-dimethylformamide and at a temperature between 0° C. and the reflux temperature of the solvent.

The compounds of formula (I) thus obtained may be subsequently separated from the reaction medium and purified according to conventional methods, for example by crystallization or chromatography.

The compounds of formula (I) thus obtained are isolated in free-base or salt form, according to conventional techniques.

The compounds of formula (II) and (IV) may be prepared according to the method described in French Patent 97 08409 or in international application WO 2004/041817.

According to this method a 2-aminoindole of formula

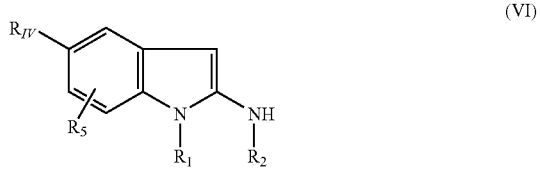

(VI)

in which $R_1$, $R_2$ and $R_5$ are as defined for a compound of formula (I) and $R_{IV}$ represents a group —$COR_{11}$ or a $(C_1-C_4)$ alkoxycarbonyl group is reacted with an ester of formula

(VII)

in which $R_3$ is as defined for a compound of formula (I) and Alk represents a $c_1-c_4$ alkyl.

The reaction is carried out in a solvent which is polar and preferably basic, for example in pyridine, at a temperature between the ambient temperature and the reflux temperature of the solvent.

It is also possible to prepare a compound of formula (II) or (IV) by another process, by reacting a 2-aminoindole of formula

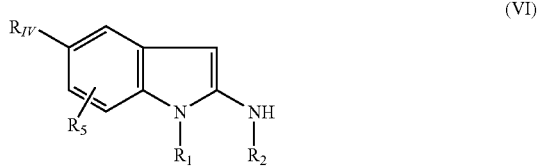

(VI)

in which $R_1$, $R_2$, $R_{IV}$ and $R_5$ are as defined above with an ester of formula

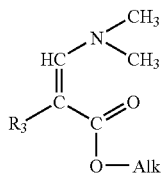

(VIII)

in which $R_3$ is as defined for a compound of formula (I) and Alk represents a $c_1$-$c_4$ alkyl.

The reaction is carried out in a protic, polar solvent, preferably in acidic medium, at a temperature between the ambient temperature and the reflux temperature of the solvent.

The preparation of the compound of formula (VIII) is carried out by means of dimethoxy-N,N-dimethylmethanamine in accordance with a method similar to that described in J. Org. Chem., 1982, 47, 2846-51 or by means of Bredereck's reagent (tert-butoxybis(dimethylamino)methane) according to Liebigs Ann. Chem., 1980, 3, 344-57.

Generally speaking, it is also possible to prepare a compound of formula

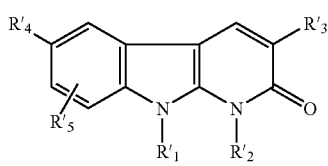

(XIV)

in which the substituents $R'_1$, $R'_2$, $R'_3$, $R'_4$ and $R'_5$ are precursors of the substituents $R_1$, $R_2$, $R_3$, $R_4$ and $R_5$ as defined for a compound of formula (I) and then, using methods known to the skilled person, to convert these substituents to give the substituents $R_1$, $R_2$, $R_3$, $R_4$ and $R_5$ that are desired for the compound of formula (I).

The compounds of formula (XIV) in which $R'_4$ is a cyano group may be converted to compounds of formula (II) in which $R_{11}$=H by the action of Raney nickel in the presence of sodium hypophosphite.

A compound of formula (II) in which $R_{11}$ represents a $(C_1$-$C_4)$alkyl may also be prepared by reacting a compound of formula (XIV) in which $R'_4$=H with a compound of formula $R_{11}$COCl, in the presence of $AlCl_3$, in a solvent such as dichloromethane and at a temperature between 0° C. and the ambient temperature.

The compounds of formula (III) are known or are prepared according to known methods.

The compounds of formula (V) are known or are prepared according to known methods.

The compounds of formula (VII) are known or are prepared according to the methods described in WO 2004/041817.

The compounds of formula (IX) are prepared by reacting a compound of formula

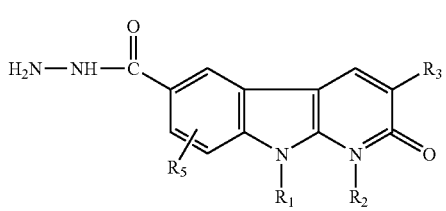

(X)

in which $R_1$, $R_2$, $R_3$ and $R_5$ are as defined for a compound of formula (I) with an acid, or a functional derivative of this acid, of formula

HOOC—$R_{14}$ in which $R_{14}$ is as defined for a compound of formula (I), according to the conventional methods of acylation.

The compounds of formula (X) are prepared from compounds of formula

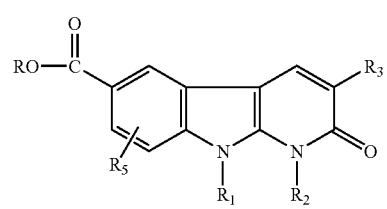

(IV)

in which $R_1$, $R_2$, $R_3$ and $R_5$ are as defined for a compound of formula (I) and R represents a hydrogen atom or a $(C_1$-$C_4)$ alkyl.

When R=H the acid of formula (IV) itself or a functional derivative of this acid is reacted with a compound of formula $H_2N$—NH-Pg    (XIII)

in which Pg represents an N-protective group such as tert-butyloxycarbonyl, according to the conventional methods of peptide coupling, and the intermediate compound obtained is deprotected according to conventional methods.

When R=$(C_1$-$C_4)$alkyl the ester of formula (IV) is reacted with hydrazine, in a solvent such as ethanol and at a temperature between the ambient temperature and the reflux temperature of the solvent.

The compounds of formula (XI) are prepared by reacting a compound of formula

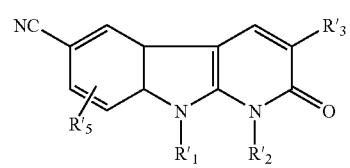

(XIV): $R'_4$ = CN in which $R'_1$, $R'_2$, $R'_3$ and $R'_5$ are as defined above with hydroxylamine, in the presence of a base such as triethylamine, in a solvent such as ethanol and at a temperature between the ambient temperature and the reflux temperature of the solvent.

The compounds of formula (XIV: $R'_4$=CN) are known and are prepared according to the methods described in WO 2004/041817.

The invention, according to another of its aspects, also provides the compounds of formula (IX), (X), (XI) and (XII). These compounds are of use as synthesis intermediates of the compounds of formula (I).

Accordingly the invention provides compounds of formula

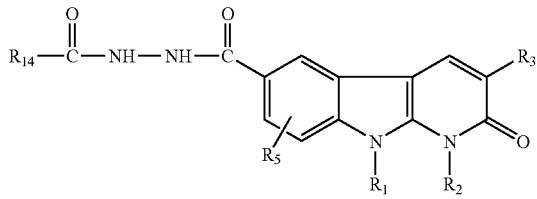

(IX)

in which
- $R_1$ represents a hydrogen atom; a $(C_1\text{-}C_4)$alkyl group; a group $-(CH_2)_m OH$; a group $-(CH_2)_m CN$; or a group $-(CH_2)_m NR_9 R_{10}$;
- $R_2$ represents a hydrogen atom or a $(C_1\text{-}C_4)$alkyl group;
- $R_3$ represents a phenyl substituted by $R_6$, $R_7$, $R_8$;
- $R_5$ represents a hydrogen atom or a $(C_1\text{-}C_4)$ alkyl group;
- $R_6$, $R_7$ and $R_8$ represent, each independently of one another, a hydrogen atom; a halogen atom; a $(C_1\text{-}C_4)$ alkyl group; a $(C_1\text{-}C_4)$alkoxy group; a hydroxyl; a cyano; a group $-(CH_2)_n NR_9 R_{10}$; or a group $-O-(CH_2)_m N_9 R_{10}$;
- $R_9$ and $R_{10}$ represent, each independently of one another, a hydrogen atom or a $(C_1\text{-}C_4)$alkyl group;
- or else $R_9$ and $R_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a $(C_1\text{-}C_4)$ alkyl;
- $R_{14}$ represents a hydrogen atom; a $(C_1\text{-}C_4)$alkyl group; or a group $-NR_{17} R_{18}$;
- $R_{17}$ and $R_{18}$ represent, each independently, a hydrogen atom or a $(C_1\text{-}C_4)$alkyl group; $R_{18}$ may also represent a group $-COR_{21}$; or a group $-SO_2 R_{22}$;
- $R_{21}$ represents a $(C_1\text{-}C_4)$alkyl group; a $(C_3\text{-}C_6)$cycloalkyl group; or a group $-(CH_2)_m NR_9 R_{10}$;
- $R_{22}$ represents a $(C_1\text{-}C_4)$alkyl group;
- m is 1, 2 or 3; and
- n is 0, 1, 2 or 3.

The invention also provides compounds of formula

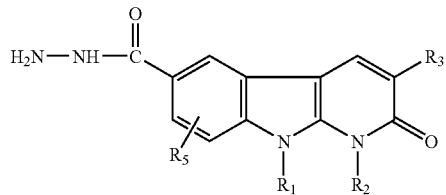

(X)

in which
- $R_1$ represents a hydrogen atom; a $(C_1\text{-}C_4)$alkyl group; a group $-(CH_2)_m OH$; a group $-(CH_2)_m CN$; or a group $-(CH_2)_m R_9 R_{10}$;
- $R_2$ represents a hydrogen atom or a $(C_1\text{-}C_4)$alkyl group;
- $R_3$ represents a phenyl substituted by $R_6$, $R_7$, $R_8$;
- $R_5$ represents a hydrogen atom or a $(C_1\text{-}C_4)$alkyl group;
- $R_6$, $R_7$ and $R_8$ represent, each independently of one another, a hydrogen atom; a halogen atom; a $(C_1\text{-}C_4)$ alkyl group; a $(C_1\text{-}C_4)$ alkoxy group; a hydroxyl; a cyano; a group $-(CH_2)_n NR_9 R_{10}$; or a group $-O-(CH_2)_m NR_{9R10}$;
- $R_9$ and $R_{10}$ represent, each independently of one another, a hydrogen atom or a $(C_1\text{-}C_4)$alkyl group;
- or else $R_9$ and $R_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a $(C_1\text{-}C_4)$ alkyl;
- m is 1, 2 or 3; and
- n is 0, 1, 2 or 3.

The invention also provides compounds of formula

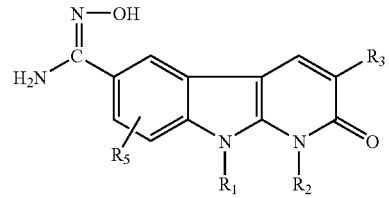

(XI)

in which
- $R_1$ represents a hydrogen atom; a $(C_1\text{-}C_4)$alkyl group; a group $-(CH_2)_m OH$; a group $-(CH_2)_m CN$; or a group $-(CH_2)_m NR_9 R_{10}$;
- $R_2$ represents a hydrogen atom or a $(C_1\text{-}C_4)$alkyl group;
- $R_3$ represents a phenyl substituted by $R_6$, $R_7$, $R_8$;
- $R_5$ represents a hydrogen atom or a $(C_1\text{-}C_4)$alkyl group;
- $R_6$, $R_7$ and $R_8$ represent, each independently of one another, a hydrogen atom; a halogen atom; a $(C_1\text{-}C_4)$ alkyl group; a $(C_1\text{-}C_4)$ alkoxy group; a hydroxyl; a cyano; a group $-(CH_2)_n NR_9 R_{10}$; or a group $-O-(CH_2)_m NR_9 R_{10}$;
- $R_9$ and $R_{10}$ represent, each independently of one another, a hydrogen atom or a $(C_1\text{-}C_4)$alkyl group;
- or else $R_9$ and $R_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a $(C_1\text{-}C_4)$alkyl;
- m is 1, 2 or 3; and
- n is 0, 1, 2 or 3.

The invention also provides compounds of formula

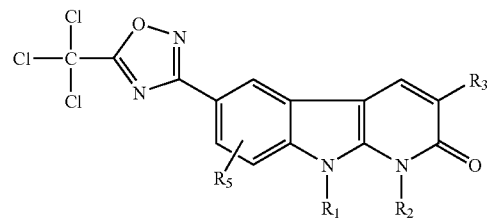

(XII)

in which
- $R_1$ represents a hydrogen atom; a $(C_1\text{-}C_4)$alkyl group; a group $-(CH_2)_m OH$; a group $-(CH_2)_m CN$; or a group $-(CH_2)_m NR_9 R_{10}$;
- $R_2$ represents a hydrogen atom or a $(C_1\text{-}C_4)$alkyl group;
- $R_3$ represents a phenyl substituted by $R_6$, $R_7$, $R_8$;
- $R_5$ represents a hydrogen atom or a $(C_1\text{-}C_4)$alkyl group;
- $R_6$, $R_7$ and $R_8$ represent, each independently of one another, a hydrogen atom; a halogen atom; a $(C_1\text{-}C_4)$ alkyl group; a $(C_1\text{-}C_4)$alkoxy group; a hydroxyl; a cyano; a group $-(CH_2)_n NR_9 R_{10}$; or a group $-O-(CH_2)_m NR_9 R_{10}$;

$R_9$ and $R_{10}$ represent, each independently of one another, a hydrogen atom or a ($C_1$-$C_4$)alkyl group;

or else $R_9$ and $R_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a ($C_1$-$C_4$) alkyl;

m is 1, 2 or 3; and n is 0, 1, 2 or 3.

In the absence of any indication to the contrary, the proton nuclear magnetic resonance spectra ($^1$H NMR) are recorded in DMSO-$d_6$; the reference is placed in DMSO-$d_6$, which is situated at 2.50 ppm from the tetramethylsilane.

The signals observed in NMR are expressed as follows: s: singlet; se: singlet, enlarged; d: doublet; dd: doublet, doubled; t: triplet; td: triplet, doubled; q: quadruplet; m: unresolved peak; mt: multiplet.

The examples which follow describe the preparation of certain compounds in accordance with the invention. These examples are not limitative and serve merely to illustrate the present invention. The numbers of the compounds exemplified match those given in the table hereinafter, which illustrates the chemical structures and physical properties of some compounds according to the invention.

In the preparations and examples below, the following abbreviations are used:

DIPEA: diisopropylethylamine
TEA: triethylamine
DMA: dimethylacetamide
DMF: dimethylformamide
PE: petroleum ether
DMFDMA: dimethylformamide dimethyl acetal
NMP: N-Me pyrrolidin-2-one
LAH: lithium aluminium hydride
THF: tetrahydrofuran
Ether: diethyl ether
DCM: dichloromethane
CDI: carbonyldiimidazole
AcOEt: ethyl acetate
AcOH: acetic acid
dppp: 1,3-tris(diphenylphosphino)propane
iPrOH: isopropyl alcohol
Bredereck's reagent: tert-butoxybis(dimethylamino)methane
DDQ: 2,3-dichloro-5,6-dicyano-1,4-benzoquinone
PyBOP: (benzotriazol-1-yl oxy)tripyrrolidinophosphonium hexafluorophosphate
AT: ambient temperature
m.p.: melting point Preparation of the compounds of formula (VI)

The compounds of formula (VI) can exist in 2 tautomeric forms:

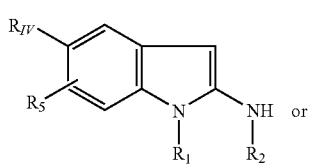 or

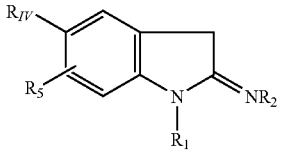

Preparation 1.1

N-Methyl-5-bromo-1H-indole-2-amine, hydrochloride.

A) N'-(4-Bromophenyl)-N-formylhydrazine.

10 g of 4-bromophenylhydrazine hydrochloride are dissolved in 30 ml of water; 6.2 g of $K_2CO_3$ and 36 ml of methyl formate are added and then the mixture is heated at reflux for 1 hour and then at AT for 12 hours. The precipitate formed is filtered off and then washed with an isopropanol/PE mixture (50/50; v/v). This gives 10.5 g of the expected compound.

NMR $CDCl_3$ (300 MHz): 6.73-6.77 ppm: m: 2H; 7.34-7.41 ppm: m: 2H; 8.33 ppm: m: 1H.

B) N-Methyl-N'-(4-bromophenyl)acetohydrazine.

A solution of 80 ml of LAH in THF is heated to reflux, 10.5 g of the compound obtained in step A, in suspension in 60 ml of THF, are added and then the mixture is heated to reflux for 15 hours. The reaction mixture is cooled and then 12 ml of water and 9 ml of 1N NaOH are added dropwise. The mixture is filtered over Celite® to remove the insoluble and then washed with AcOEt and the reaction mixture is evaporated to dryness. The residue is taken up in 80 ml of AcOH, and 17 g of $K_2CO_3$ in 80 ml of water and then 4 ml of acetic anhydride are added and the mixture is left with stirring at AT for 1 hour. It is decanted and then the organic phase is dried over $MgSO_4$ and evaporated to dryness. Petroleum ether is added and then the crystals formed are filtered off to give 9 g of the expected compound.

NMR $CDCl_3$ (300 MHz): 2.15 ppm: s: 3H; 3.13 ppm: s: 3H; 6.57-6.62 ppm: m: 2H; 7.32-7.40 ppm: m: 2H.

C) N-Methyl-5-bromo-1H-indole-2-amine, hydrochloride.

9 g of the compound from the preceding step are dissolved in 50 ml of $POCl_3$ and the solution is heated at 80° C. for 2 hours. Following return to AT, ether is added and the precipitate formed is filtered off and then washed with ether. This gives 8.2 g of the expected compound.

NMR $CDCl_3$ (300 MHz): 4.31 ppm: s: 3H; 7.14-7.87 ppm: m: 4H; 10.70 ppm: m: 1H; 12.62 ppm: s: 1H.

Preparation 1.2

Methyl 1-methyl-2-(methylamino)-1H-indole-5-carboxylate.

A) Methyl 4-(2-acetylhydrazino)benzoate.

5.5 g of methyl 4-hydrazinobenzoate are dissolved in 38.2 ml of AcOH containing 2.4 g of sodium acetate and the solution is heated at 80° C. for 18 hours. The inorganic material is removed by suction filtration and then evaporation is carried out and the residue is taken up in a minimum of $Et_2O$. Suction filtration gives 7.97 g of the expected compound.

B) Methyl 4-(2-acetyl-1,2-dimethylhydrazino)benzoate.

2.95 g of 95% NaH are suspended in 90 ml of DMF, and the suspension is admixed dropwise with 8.135 g of the compound from the preceding step, in solution in a minimum of DMF, and then, after a few minutes, 9.75 ml of methyl iodide are added dropwise. The mixture is stirred at AT for 1 hour. The mixture is poured into saturated $NH_4Cl$ solution and extracted with AcOEt. The organic phase is washed with NaCl, dried and evaporated to give 5.4 g of the expected compound.

C) Methyl 1-methyl-2-(methylamino)-1H-indole-5-carboxylate.

5.4 g of the compound from the preceding step and 62 ml of phosphorus oxychloride are mixed and the mixture is heated for 2½ hours at 80° C. The mixture is evaporated and the residue is taken up in AcOEt. The solid formed is filtered off with suction, washed with AcOEt and dried to give 4 g of the expected compound.

NMR MeOD (250 MHz): 3.2 ppm: s: 3H; 3.6 ppm: s: 3H; 3.9 ppm: s: 3H; 7.3-7.4 ppm: m: 2H; 8.1-8.2 ppm: m: 2H.

Preparation 1.3

Methyl 2-(methylamino)-1H-indole-5-carboxylate.

A) Methyl 4-(2-acetyl-2-methylhydrazino)benzoate.

10 g of the compound from Preparation 1.2, step A are dissolved in 60 ml of anhydrous DMF and the solution is cooled to 0° C. In small portions, 1.9 g of 60% NaH are added and stirring is maintained until the evolution of gas has ceased. 4.5 ml of $CH_3I$ are added and the mixture is stirred at 0° C. for 20 minutes. The reaction mixture is poured into saturated $NH_4Cl$ solution and then extracted with AcOEt. The organic phase is washed with saturated NaCl solution, dried over $MgSO_4$ and then purified by chromatography on silica, eluting with AcOEt/cyclohexane (50/50; v/v then 75/25; v/v). This gives 6.2 g of the expected compound.

NMR DMSO (300 MHz): 2.15 ppm: s: 3H; 3.17 ppm: s: 3H; 3.89 ppm: s: 3H; 6.11 ppm: s: 1H; 6.71 ppm: d: 2H; 7.98 ppm: d: 2H.

B) Methyl 2-(methylamino)-1H-indole-5-carboxylate.

5.3 g of the compound from the preceding step are dissolved in 30 ml of $POCl_3$ and the solution is heated at 80° C. for 2 hours. After the reaction mixture has been cooled, ether is added and the mixture is stirred. The precipitate formed is filtered off and then washed with ether to give 3.2 g of the expected compound.

NMR DMSO(300 MHz): 3.08 ppm: s: 3H; 3.85 ppm: s: 3H; 4.25 ppm: s: 2H; 6.29 ppm: d: 1H; 8 ppm: m: 2H; 10.78 ppm: s: 1H; 12.64 ppm: s: 1H.

Preparation 1.4

1-Methyl-2-(methylamino)-1H-indole-5-carbonitrile.

A) N'-(4-Cyanophenyl)acetohydrazide.

A solution of 5 g of 4-cyanophenylhydrazine hydrochloride in 40 ml of acetic acid is admixed with 2.7 g of sodium acetate and then heated at 80° C. for 20 hours. The reaction mixture is concentrated under vacuum, the residue is taken up in water and extracted with AcOEt, the organic phase is washed with saturated NaCl solution and dried over $MgSO_4$ and the solvent is evaporated under vacuum. The residue is triturated in a PE/AcOEt mixture (90/10; v/v) and the precipitate formed is filtered off with suction. This gives 4.8 g of the expected compound.

$^1$H NMR: $CDCl_3$ (300 MHz): δ (ppm) : 1.92: s: 3H; 6.75: d: 2H; 7.53: d: 2H; 8.25: s: 1H; 9.76: s: 1H.

B) N'-(4-Cyanophenyl)-N,N'-dimethylacetohydrazide.

A suspension of 2.8 g of 60% NaH in oil in 50 ml of DMF is admixed, dropwise and at AT, with a solution of 4.8 g of the compound obtained in the preceding step in 20 ml of DMF, and stirring is maintained until the evolution of gas is at an end. Subsequently 6.8 ml of methyl iodide are added and then stirring is maintained at AT for 2 hours. The reaction mixture is poured into saturated $NH_4Cl$ solution and extracted with AcOEt, the organic phase is washed with saturated NaCl solution and dried over $MgSO_4$ and the solvent is evaporated under vacuum. The residue is taken up in PE and the precipitate formed is filtered off with suction. This gives 4.5 g of the expected compound.

$^1$H NMR: $CDCl_3$ (300 MHz): δ (ppm): 2.04: s: 3H; 3.03: s: 3H; 3.21: s: 3H; 6.70: d: 3H; 7.57: d: 2H.

C) 1-Methyl-2-(methylamino)-1H-indole-5-carbonitrile.

A solution of 4.0 g of the compound obtained in the preceding step in 30 ml of $POCl_3$ is heated at 75° C. for 1 hour 30 minutes. After cooling to AT, the precipitate formed is filtered off with suction and washed with ether. This gives 3.4 g of the expected compound.

Preparation 1.5

N,1-Dimethyl-1H-indol-2-amine.

This compound is prepared according to the procedures described in WO 2004/041817, m.p.=249° C.

Preparation of the Compounds of Formula (VII) or (VIII).

Preparation 2.1

Ethyl 2-(3-bromophenyl)-3-hydroxy-2-propenoate (VII).

A) Ethyl 3-bromophenylacetate.

5 g of 3-bromophenylacetic acid are dissolved in 80 ml of ethanol, 3 ml of concentrated $H_2SO_4$ are added and then the solution is heated at reflux for 2 hours. The ethanol is evaporated and the residue is neutralized with saturated $K_2CO3$ solution and then extracted with AcOEt and dried over $MgSO_4$. This gives 5.2 g of the expected compound in liquid form.

NMR $CDCl_3$ (300 MHz): 1.18 ppm: t: 3H; 3.50 ppm: s: 2H; 4.08 ppm: q: 2H; 7.09-7.37 ppm: m: 4H.

B) Ethyl 2-(3-bromophenyl)-3-hydroxy-2-propenoate.

5.2 g of the compound from the preceding step are dissolved in 70 ml of ethyl formate and, in small portions, 1.7 g of 60% NaH are added. Stirring is maintained at AT for 5 hours. The mixture is poured into 100 ml of 1N HCl and then extracted with AcOEt, and the extract is dried over $MgSO_4$ and then evaporated to dryness. This gives 5.8 g of the expected compound in the form of an oil.

NMR $CDCl_3$ (300 MHz): 1.9 ppm: t: 3H; 4.20 ppm: q: 2H; 7.11-7.42 ppm: m: 5H; 12.06 ppm: d: 1H.

Preparation 2.2

Ethyl 2-(2,4-dimethylphenyl)-3-dimethylaminoacrylate (VIII).

A) 1-Bromomethyl-2,4-dimethylbenzene.

5 g of (2,4-dimethylphenyl)methanol are dissolved in 100 ml of ether. The reaction mixture is cooled to 0° C. It is admixed dropwise with 5.2 ml of phosphorus tribromide. It is stirred at ambient temperature overnight. The reaction mixture is poured onto ice and extracted with AcOEt. The organic phase is washed with saturated NaCl solution. The organic phase is dried over $MgSO_4$, filtered and evaporated to dryness. This gives 7.3 g of the expected compound.

NMR $CDCl_3$ (300 MHz): 2.28 ppm: s: 3H; 2.35 ppm: s: 3H; 4.48 ppm: s: 2H; 6.90-7.22 ppm: m: 3H.

B) (2,4-Dimethylphenyl)acetonitrile.

7.3 g of the compound from the preceding step are dissolved in 120 ml of ethanol and 30 ml of water. 4.7 g of potassium cyanide are added. The mixture is heated at reflux for 5 hours. The ethanol is evaporated and the residue is taken up in water. It is extracted with AcOEt and then the organic phase is washed with saturated NaCl solution. The organic phase is dried over $MgSO_4$, filtered and evaporated to dryness. This gives 5.3 g of the expected compound.

NMR $CDCl_3$ (300 MHz): 2.37 ppm: s: 6H; 3.68 ppm: s: 2H; 7.00-7.32 ppm: m: 3H.

C) Ethyl (2,4-dimethylphenyl)acetate.

5.3 g of the compound 2.2, step B are dissolved in 120 ml of ethanol and 7 ml of $H_2SO_4$. The solution is heated at reflux for 10 days. The ethanol is evaporated and the residue is taken up in saturated $K_2CO_3$ solution. It is extracted with AcOEt and the organic phase is washed with saturated NaCl solution. The organic phase is dried over $MgSO_4$, filtered and evaporated to dryness. This gives 6.0 g of a yellow oil.

NMR $CDCl_3$ (300 MHz): 1.25 ppm: t: 3H; 2.27 ppm: 2s: 6H; 3.56 ppm: s: 2H; 4.14 ppm: q: 2H; 6.91-7.27 ppm: m: 3H.

D) Ethyl 2-(2,4-dimethylphenyl)-3-dimethylaminoacrylate.

6.0 g of the compound from the preceding step are dissolved in 9 ml of Bredereck's reagent. The solution is heated at 100° C. for 15 hours. It is evaporated to dryness. It is purified on a silica column eluted with an AcOEt/cyclohexane mixture (10/90; v/v). This gives 6.7 g of a yellow oil.

NMR $CDCl_3$ (300 MHz): 1.21 ppm: t: 3H; 2.16 ppm: s: 3H; 2.29 ppm: s: 3H; 2.60 ppm: s: 6H; 4.09 ppm: q: 2H; 6.90-7.57 ppm: m: 4H.

Following procedures according to the Preparations described above, the intermediates of formula (VII) or (VIII) collated in the table below are obtained.

TABLE 1

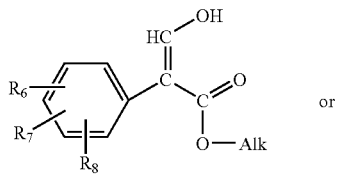

(VII)

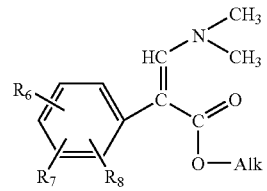

(VIII)

| Preparations | $R_6, R_7, R_8$ | Intermediate (VII) or (VIII) | Characterization |
|---|---|---|---|
| 2.3 | 2,4-diCl | (VII): Alk = Et (VIII): Alk = Me | NMR $CDCl_3$ (300 MHz): 1.25 ppm: t: 3H; 4.25 ppm: q: 2H; 7.13-7.44 ppm: m: 4H; 12.03 ppm: m: 1H. m.p. = 73° C. |
| 2.4 | 2,4-diOMe | (VIII): Alk = Me | NMR DMSO (300 MHz): 2.62 ppm: s: 6H; 3.44 ppm: s: 3H; 3.69 ppm: s: 3H; 3.75 ppm: s: 3H; 6.40-6.48 ppm: m: 2H; 6.87 ppm: d: 1H; 7.41 ppm: s: 1H. |
| 2.5 | H | (VII): Alk = Me | Described in J. Am. Chem. Soc., 1974, 96, 2127-9 |
| 2.6 | 3-Br | (VIII): Alk = Me | NMR DMSO (300 MHz): 2.66 ppm: s: 6H; 3.50 ppm: s: 3H; 7.10-7.52: m: 5H. |
| 2.7 | 2-Cl | (VII): Alk = Et | $^1$H NMR: $CDCl_3$ (300 MHz): δ (ppm): 1.24: t: 3H; 4.25: q: 2H; 7.15-7.50: m: 4H; 12.0: d: 1H. |
| 2.8 | 4-Cl | (VIII): Alk = Me | $^1$H NMR: $CDCl_3$ (300 MHz): δ (ppm): 2.57: s: 6H; 3.51: s: 3H; 6.98-7.44: m: 5H. |
| 2.9 | 3-Br | (VIII): Alk = Et | |
| 2.10 | 4-Br | (VIII): Alk = Et | m.p. = 97° C. |
| 2.11 | 3-F | (VIII): Alk = Me | NMR: $CDCl_3$ (300 MHz): δ (ppm): 2.66: s: 6H; 3.50: s: 3H; 6.90-7.31: m: 4H; 7.52: s: 1H. |
| 2.12 | 4-F | (VIII): Alk = Et | |
| 2.13 | 3-Me | (VIII): Alk = Me | $^1$H NMR: $CDCl_3$ (300 MHz): δ (ppm): 2.33: s: 3H; 2.66: s: 6H; 3.61: s: 3H; 7.04-7.25: m: 4H; 7.54: s: 1H. |
| 2.14 | 3-OMe | (VII): Alk = Et | $^1$H NMR: $CDCl_3$ (300 MHz): δ (ppm): 1.35: t: 3H; 3.85: s: 3H; 4.34: q: 2H; 6.7-7.0: m: 2H; 7.2-7.4: m: 3H; 12.18: d: 1H. |
| 2.15 | 4-OMe | (VII): Alk = Et | $^1$H NNR: $CDCl_3$ (300 MHz): δ (ppm): 1.25: t: 3H; 3.86: s: 3H; 4.33: q: 2H; 6.92: d: 2H; 7.23: d: 2H; 7.28: d: 1H; 12.08: d: 1H. |
| 2.16 | 3-CN | (VIII): Alk = Et | |
| 2.17 | 4-CN | (VIII): Alk = Et | |
| 2.18 | 3,5-diF | (VIII): Alk = Me | $^1$H NMR: DMSO-$d_6$ (300 MHz): δ (ppm): 2.70: s: 6H; 3.52: s: 3H; 6.79-7.08: m: 3H; 7.53: s: 1H. |
| 2.19 | 2-OMe | (VII): Alk = Et | $^1$H NMR: $CDCl_3$ (300 MHz) δ (ppm): 1.24: t: 3H; 3.78: s: 3H; 4.22: q: 2H; 6.85-7.00: m: 2H; 7.10-7.40: m: 2H; 11.91: d: 1H. |

Preparation 2.20

Ethyl 3-(dimethylamino)-2-[4-(2-morpholin-4-ylethoxy) phenyl]acrylate.

A) Ethyl [4-(2-morpholin-4-ylethoxy)phenyl]acetate.

A solution of 1 g of ethyl (4-hydroxyphenyl)acetate in 20 ml of EtOH is admixed with 2.5 g of $K_2CO_3$, 1.68 g of 4-(2-chloroethyl)morpholine hydrochloride and 0.01 g of tetrabutylammonium iodide and then heated at reflux for 5 hours. After cooling to AT, the $K_2CO_3$ is filtered off and washed with EtOH and the filtrate is concentrated under vacuum. The residue is taken up in water and extracted with AcOEt, the organic phase is washed with water and dried over $MgSO_4$ and the solvent is evaporated under vacuum. This gives 1.5 g of the expected compound in the form of a colourless oil.

¹H NMR: DMSO-d₆ (300 MHz): δ (ppm): 1.17: t: 3H; 2.44: m: 4H; 2.67: t: 2H; 3.53-3.59: m: 6H; 4.02-4.09: m: 4H; 6.88: d: 2H; 7.15: d: 2H.

B) Ethyl 3-(dimethylamino)-2-[4-(2-morpholin-4-yl-ethoxy)phenyl]acrylate.

A mixture of 1.5 g of the compound obtained in the preceding step in 1 ml of Bredereck's reagent is heated at 100° C. overnight. After cooling to AT, it is admixed with EtOH and concentrated under vacuum. This gives 1.9 g of the expected compound in the form of orange-coloured oil.

Preparations of the Compounds of Formula (XIV), (X) and (XI).

Preparation 3.1

3-(2,4-Dimethoxyphenyl)-1-methyl-2-oxo-2,9-dihydro-1H-pyrido[2,3-b]indole-6-carbaldehyde.

A) 6-Bromo-3-(2,4-dimethoxyphenyl)-1-methyl-1,9-dihydropyrido[2,3-b]indol-2-one.

4.0 g of compound from Preparation 1.1 are dissolved in 30 ml of acetic acid. The solution is heated at 100° C. for 15 minutes and then 3.6 g of the compound from Preparation 2.4 are added. The mixture is heated at reflux for 2 hours 30 minutes. The reaction mixture is cooled and then the precipitate formed is filtered off. This gives 3.3 g of the expected compound.

NMR DMSO (300 MHz): 3.58 ppm: s: 3H; 3.65 ppm: s: 3H; 3.80 ppm: s: 3H; 6.53 ppm: dd: 1H; 6.60 ppm: s: 1H; 7.10 ppm: d: 1H; 7.29 ppm: d: 1H; 7.43 ppm: d: 1H; 8.04 ppm: s: 2H; 12.21 ppm: s: 1H.

B) 3-(2,4-Dimethoxyphenyl)-1-methyl-2-oxo-2,9-dihydro-1H-pyrido[2,3-b]indole-6-carbonitrile.

3.0 g of the compound from the preceding step are dissolved in 70 ml of NMP. 1.3 g of CUCN are added and then the mixture is heated at 200° C. for 24 hours. The reaction mixture is poured into water and the product is extracted with AcOEt. It is purified by chromatography on a silica column, eluting with pure AcOEt and then with AcOEt/MeOH (98/2; v/v). This gives 0.82 g of beige powder.

NMR DMSO (300 MHz): 3.66 ppm: s: 3H; 3.70 ppm: s: 3H; 3.80 ppm: s: 3H; 6.55 ppm: dd: 1H; 6.62 ppm: d: 1H; 7.13 ppm: d: 1H; 7.55-7.62 ppm: m: 2H; 8.10 ppm: s: 1H; 8.37 ppm: s: 1H; 12.53 ppm: s: 1H.

C) 3-(2,4-Dimethoxyphenyl)-1-methyl-2-oxo-2,9-dihydro-1H-pyrido[2,3-b]indole-6-carbaldehyde.

0.4 g of the compound from the preceding step is dissolved in 30 ml of pyridine, 10 ml of acetic acid and 6 ml of water. 2.6 g of NaH₂PO₂ and 2.0 g of Raney nickel are added. The mixture is heated at 65° C. for 40 hours. The catalyst is filtered off hot on Celite, the filtrate is washed with methanol and evaporated to dryness and the residue is taken up in AcOEt and then washed with saturated NaCl solution. It is dried over MgSO₄ and then purified by chromatography on a silica column, eluting with AcOEt and then AcOEt/MeOH (98/2; v/v). This gives 160 mg of the expected compound.

NMR DMSO (300 MHz): 3.67 ppm: s: 3H; 3.70 ppm: s: 3H; 3.80 ppm: s: 3H; 6.55 ppm: d: 1H; 6.62 ppm: s: 1H; 7.16 ppm: d: 1H; 7.61 ppm: d: 1H; 7.75 ppm: d: 1H; 8.13 ppm: S: 1H; 8.43 ppm: S: 1H; 10.00 ppm: S: 1H; 12.47 ppm: s: 1H.

Preparation 3.2

Ethyl 3-(2,4-dimethoxyphenyl)-1,9-dimethyl-2-oxo-2,9-dihydro-1H-pyrido[2,3-b]indole-6-carboxylate.

A) 3-(2,4-Dimethoxyphenyl)-1-methyl-2-oxo-2,9-dihydro-1H-pyrido[2,3-b]indole-6-carboxylic acid.

5.0 g of KOH are dissolved in 15 ml of H₂O and then 2.2 g of the compound from Preparation 3.1, step B and 1.1 ml of aqueous 35% H₂O₂ solution are added. The mixture is heated at 130° C. for 2 days. The reaction mixture is cooled and then water is added. It is extracted with AcOEt and then the aqueous phase is acidified with 1N HCl solution. The precipitate formed is filtered off, washed with water and then taken up in a 50/50 AcOEt/MeOH mixture. It is dried over MgSO₄ and then evaporated to dryness. This gives 1.1 g of the expected compound in the form of a powder.

NMR DMSO (300 MHz): 3.67 ppm: s: 3H; 3.70 ppm: s: 3H; 3.80 ppm: s: 3H; 6.54 ppm: d: 1H; 6.61 ppm: s: 1H; 7.19 ppm: d: 1H; 7.41 ppm: d: 1H; 7.90-7.96 ppm: m: 2H; 8.42 ppm: s: 1H.

B) Ethyl 3-(2,4-dimethoxyphenyl)-1-methyl-2-oxo-2,9-dihydro-1H-pyrido[2,3-b]indole-6-carboxylate.

0.4 g of the compound from the preceding step is dissolved in 30 ml of ethanol and 0.5 ml of concentrated H₂SO₄. The solution is heated at reflux for 5 hours. The ethanol is evaporated and the residue is neutralized with saturated K₂CO₃ solution and then extracted with AcOEt. It is purified by chromatography on a silica column eluted with AcOEt. This gives 0.21 g of the expected compound in the form of powder.

NMR DMSO (300 MHz): 1.36 ppm: t: 3H; 3.67 ppm: s: 3H; 3.70 ppm: s: 3H; 3.80 ppm: s: 3H; 4.32 ppm: q: 2H; 6.52-6.56 ppm: dd: 1H; 6.61 ppm: d: 1H; 7.16 ppm: d: 1H; 7.54 ppm: d: 1H; 8.15 ppm: s: 1H; 8.49 ppm: s: 1H; 8.83 ppm: d: 1H; 12.33 ppm: s: 1H.

C) Ethyl 3-(2,4-dimethoxyphenyl)-1,9-dimethyl-2-oxo-2,9-dihydro-1H-pyrido[2,3-b]indole-6-carboxylate.

15 mg of 60% NaH are suspended in 5 ml of DMF. 0.1 g of the compound from Preparation 3.2, step B is added, followed, at the end of evolution of gas, by 0.03 ml of CH₃I. The mixture is stirred at AT for 1 hour. The reaction mixture is poured into water, the white precipitate formed is filtered off and washed with water and then the precipitate is taken up in AcOEt and a little methanol. It is dried over MgSO₄ and then evaporated to dryness. The precipitate is taken up in an AcOEt/PE mixture (10/90; v/v) and filtered off. This gives 0.1 g of the expected compound.

NMR DMSO (300 MHz): 1.35 ppm: t: 3H; 3.70 ppm: s: 3H; 3.81 ppm: s: 3H; 3.94 ppm: s: 3H; 3.99 ppm: s: 3H; 4.32 ppm: q: 2H; 6.54-6.57 ppm: dd: 1H; 6.62 ppm: d: 1H; 7.16 ppm: d: 1H; 7.68 ppm: d: 1H; 7.85-7.89 ppm: dd: 1H; 8.18 ppm: s: 1H; 8.49 ppm: s: 1H.

Preparation 3.3

Methyl 3-(2,4-dimethylphenyl)-1-methyl-2-oxo-2,9-dihydro-1H-pyrido[2,3-b]indole-6-carboxylate.

1.3 g of the compound from Preparation 1.3 are dissolved in 10 ml of glacial AcOH, the solution is heated to 110° C. and then 1.18 g of the compound from Preparation 2.2 are added and heating is maintained at 110° C. overnight. The mixture is extracted with AcOEt and the organic phase is dried over MgSO₄, filtered and evaporated to dryness. The residue is chromatographed on silica, eluting with an AcOEt/cyclohexane mixture (75/25; v/v). This gives 100 mg of the expected compound.

NMR DMSO (300 MHz): 2.14 ppm: s: 3H; 2.31 ppm: s: 3H; 3.70 ppm: s: 3H; 3.86 ppm: s: 3H; 7.04 ppm: m: 3H; 7.55 ppm: d: 1H; 7.85 ppm: dd: 1H; 8.18 ppm: s: 1H; 8.53 ppm: s: 1H; 12.40 ppm: s: 1H.

Operating as described in Preparations 3 above, the intermediates of formula (II') or (IV') collated in the table below are prepared.

TABLE 2

(XIV)

Structure: pyrido-indolone core with R'4 on benzene ring, R'1 on indole N, Me on pyridone N, and phenyl substituent bearing R'6, R'7, R'8.

| Preparations | R'1 | R'6, R'7, R'8 | R'4 | Characterization |
|---|---|---|---|---|
| 3.4 | H | H | —CHO | m.p. = 240° C. |
| 3.5 | H | 2,4-diCl | —COOMe | DMSO (300 MHz): 3.69 ppm: s: 3H; 3.86 ppm: s: 3H; 7.41-7.48 ppm: m: 2H; 7.54 ppm: d: 1H; 7.66 ppm: s: 1H; 7.85 ppm: d: 1H; 8.33 ppm: s: 1H; 8.54 ppm: s: 1H; 12.48 ppm: s: 1H. |
| 3.6 | Me | 2,4-diMe | —COOMe | m.p. = 257° C. |
| 3.7 | Me | H | —COOMe | m.p. = 128° C. |
| 3.8 | Me | 2-Me, 5-F | —COOMe | DMSO-$d_6$ (300 MHz): δ (ppm): 2.15: s: 3H; 3.87: s: 3H; 4.03: s: 3H; 4.20: s: 3H; 7.02-7.11: m: 2H; 7.28: t: 1H; 7.73: d: 1H; 7.90: dd: 1H; 8.35: s: 1H; 8.58: d: 1H. |
| 3.9 | Me | 3-F, 4-Me | —COOMe | DMSO-$d_6$ (300 MHz) δ (ppm): 2.27: s: 3H; 3.88: s: 3H; 4.02: s: 3H; 4.18: s: 3H; 7.29: t: 1H; 7.60-7.72: m: 3H; 7.89: dd: 1H; 8.66: d: 1H; 8.70: s: 1H. |
| 3.10 | H | H | —COOEt | DMSO-$d_6$ (200 MHz): δ (ppm): 1.45: t: 3H; 3.6: s: 3H; 3.8: s: 3H; 4.4: q: 2H; 7.3-7.5: m: 3H; 7.6: d: 1H; 7.8-8.0: m: 3H; 8.6: 5: 1H; 8.7: s: 1H. |
| 3.11 | H | 3-Me, 4-F | —COOMe | DMSO-$d_6$ (300 MHz): δ (ppm): 2.35: s: 3H; 3.77: s: 3H; 3.93: s: 3H; 7.20: t: 1H; 7.60: d: 1H; 7.70-7.77: m: 2H; 7.91: d: 1H; 8.60: s: 1H; 8.66: s: 1H; 12.49: s: 1H. |
| 3.12 | Me | 2-Cl | —COOMe | DMSO-$d_6$ (300 MHz): δ (ppm): 3.84: s: 3H; 4.00: s: 3H; 4.19: s: 3H; 7.38: se: 3H; 7.50: se: 1H; 7.71: d: 1H; 7.87: d: 1H; 8.35: s: 1H; 8.55: s: 1H. |
| 3.13 | Me | 4-Cl | —COOMe | DMSO-$d_6$ (300 MHz): δ (ppm): 3.87: s: 3H; 3.97: s: 3H; 4.12: s: 3H; 7.42: d: 2H; 7.63: d: 1H; 7.84: d: 3H; 8.57: s: 1H; 8.59: s: 1H. |
| 3.14 | Me | 3-Br | —COOMe | DMSO-$d_6$ (300 MHz): δ (ppm): 3.88: s: 3H; 4.01: s: 3H; 4.17: s: 3H; 7.37: t: 1H; 7.47: m: 1H; 7.70: d: 1H; 7.81-7.95: m: 2H; 8.08: d: 1H; 8.65: d: 1H; 8.72: s: 1H. |

TABLE 2-continued (XIV)

[Structure: tricyclic indole-fused pyridinone with R'₄ on benzene ring, R'₁ on indole N, Me on pyridinone N, and 3-aryl substituent with R'₆, R'₇, R'₈]

| Preparations | R'₁ | R'₆, R'₇, R'₈ | R'₄ | Characterization |
|---|---|---|---|---|
| 3.15 | Me | 4-Br | —COOMe | m.p. = 227° C. |
| 3.16 | Me | 3-F | —COOMe | DMSO-$d_6$ (300 MHz): δ (ppm): 3.88: s: 3H; 4.03: s: 3H; 4.18: s: 3H; 7.08-7.14: m: 1H; 7.40-7.47: m: 1H; 7.70-7.75: m: 3H; 7.90: dd: 1H; 8.66: d: 1H; 8.73: s: 1H. |
| 3.17 | Me | 4-F | —COOMe | DMSO-$d_6$ (300 MHz): δ (ppm): 3.88: s: 3H; 4.02: s: 3H; 4.17: s: 3H; 7.22: t: 2H; 7.70: d: 1H; 7.80-7.95: m: 3H; 8.62: t: 2H. |
| 3.18 | Me | 3-Me | —COOMe | DMSO-$d_6$ (300 MHz): δ (ppm): 2.36: s: 3H; 3.86: s: 3H; 3.97: s: 3H; 4.12: s: 3H; 7.09: d: 1H; 7.27: t: 1H; 7.58-7.65: m: 3H; 8.86: d: 1H; 8.51: s: 1H; 8.57: s: 1H. |
| 3.19 | Me | 3-OMe | —COOMe | DMSO-$d_6$ (300 MHz): δ (ppm): 3.81: s: 3H; 3.87: s: 3H; 4.01: s: 3H; 4.17: s: 3H; 6.88: d: 1H; 7.30: t: 1H; 7.40: m: 2H; 7.68: d: 1H; 7.88: d: 1H; 8.61-8.64: m: 2H. |
| 3.20 | Me | 4-OMe | —COOMe | DMSO-$d_6$ (300 MHz): δ (ppm): 3.79: s: 3H; 3.88: s: 3H; 4.02: s: 3H; 4.17: s: 3H; 6.95: d: 2H; 7.68-7.76: m: 3H; 7.88: dd: 1H; 8.53: s: 1H; 8.62: s: 1H. |
| 3.21 | Me | 3-CN | —COOMe | DMSO-$d_6$ (300 MHz): δ (ppm): 3.96: s: 3H; 4.10: s: 3H; 4.17: s: 3H; 7.41: d: 1H; 7.53: m: 1H; 7.59: m: 1H; 7.98: d: 1H; 8.07: m: 2H; 8.18: s: 1H; 8.50: s: 1H. |
| 3.22 | Me | 4-CN | —COOMe | m.p. = 263° C. |
| 3.23 | Me | 4-OCH₂CH₂—N(morpholine) | —COOMe | DMSO-$d_6$ (300 MHz): δ (ppm): 2.6: s: 4H; 2.72: t: 2H; 3.59: m: 4H; 3.93: s: 3H; 4.01: s: 3H; 4.15: m: 5H; 6.96: d: 2H; 7.68-7.73: m: 3H; 7.88: d: 1H; 8.51: s: 1H; 8.61: s: 1H. |
| 3.24 | Me | 3,5-diF | —COOMe | DMSO-$d_6$ (300 MHz): δ (ppm): 3.89: s: 3H; 4.03: s: 3H; 4.19: s: 3H; 7.08-7.15: m: 1H; 7.69-7.74: m: 3H; 7.92: dd: 1H; 8.69: s: 1H; 8.88: s: 1H. |

TABLE 2-continued (XIV)

|  |  |  |  |  |
|---|---|---|---|---|
| Preparations | R'$_1$ | R'$_6$, R'$_7$, R'$_8$ | R'$_4$ | Characterization |
| 3.25 | Me | 2-OMe | —COOMe | DMSO-d$_6$ (300 MHz): δ (ppm): 3.71: s: 3H; 3.86: s: 3H; 3.99: s: 3H; 4.18: s: 3H; 6.97: t: 1H; 7.03: d: 1H; 7.24: d: 1H; 7.31: t: 1H; 7.70: d: 1H; 7.86: d: 1H; 8.24: s: 1H; 8.52: s: 1H. |

Preparation 3.26

Methyl 3-(2,4-dichlorophenyl)-1,9-dimethyl-2-oxo-2,9-dihydro-1H-pyrido[2,3-b]indole-6-carboxylate.

A mixture of 25.47 g of the compound obtained in Preparation 1.2 and 27.4 g of the compound obtained in Preparation 2.3 (VIII) in 100 ml of acetic acid is heated at 100° C. for 2 hours. The hot reaction mixture is poured into 500 ml of an water/ice mixture and the precipitate formed is filtered off with suction, washed with water and the ether and dried. This gives 22 g of the expected compound.

Preparation 3.27

3-(2,4-Dichlorophenyl)-1,9-dimethyl-2-oxo-2,9-dihydro-1H-pyrido[2,3-b]indole-6-carbaldehyde.

A) 3-(2,4-Dichlorophenyl)-1,9-dimethyl-2-oxo-2,9-dihydro-1H-pyrido[2,3-b]indole-6-carbonitrile.

A mixture of 0.4 g of the compound obtained in Preparation 1.4 in 4 ml of acetic acid is heated at 100° C. for 15 minutes and then 0.43 g of the compound obtained in Preparation 2.3 (VIII) is added and the mixture is heated at 100° C. for 3 hours. After cooling to AT, the reaction mixture is admixed with water and the beige precipitate formed is filtered off with suction and washed with water. The precipitate is taken up in MeOH and the solvent is concentrated under vacuum. This gives 0.5 g of the expected compound.

$^1$H NMR: DMSO-d$_6$ (300 MHz): δ (ppm): 4.02: s: 3H; 4.21: s: 3H; 7.42-7.51: m: 2H; 7.66-7.70: m: 2H; 7.83: d: 1H; 8.31: s: 1H; 8.42: s: 1H.

B) 3-(2,4-Dichlorophenyl)-1,9-dimethyl-2-oxo-2,9-dihydro-1H-pyrido[2,3-b]indole-6-carbaldehyde.

A solution of 0.45 g of the compound obtained in the preceding step in 30 ml of pyridine, 10 ml of acetic acid and 6 ml of water is admixed with 3.4 g of NaH$_2$PO$_2$ and 1.7 ml of Raney® nickel and heated at 65° C. for 36 hours. The catalyst is filtered off and washed with MeOH and the filtrate is concentrated under vacuum. The residue is taken up in water and extracted with AcOEt, the organic phase is washed with saturated NaCl solution and dried over MgSO$_4$ and the solvent is evaporated under vacuum. The residue is taken up in an AcOEt/PE mixture (50/50; v/v) and the precipitate formed is filtered off with suction. This gives 0.2 g of the expected compound.

Preparation 3.28

Methyl 3-(2,4-dimethoxyphenyl)-1,9-dimethyl-2-oxo-2,9-dihydro-1H-pyrido[2,3-b]indole-6-carboxylate.

A solution of 1.83 g of the compound obtained in Preparation 1.2 in 9 ml of acetic acid is heated at 110° C. for 10 minutes and then 2 g of the compound obtained in Preparation 2.4 (VIII) are added and the mixture is heated at 110° C. for 12 hours. After cooling to AT, it is admixed with water and the precipitate formed is filtered off with suction, washed with water and then with a PE/propan-2-ol mixture (50/50; v/v) and dried under vacuum. This gives 2.76 g of the expected compound.

$^1$H NMR: DMSO-d$_6$ (300 MHz): δ (ppm): 3.71: s: 3H; 3.81: s: 3H; 3.86: s: 3H; 3.99: s: 3H; 4.19: s: 3H; 6.56: dd: 1H; 6.62: d: 1H; 7.16: d: 1H; 7.70: d: 1H; 7.87: dd: 1H; 8.19: s: 1H; 8.51: d: 1H.

Preparation 3.29

Methyl 3-[4-[[bis(4-methoxybenzyl)amino]methyl]phenyl]-1,9-dimethyl-2-oxo-2,9-dihydro-1H-pyrido[2,3-b]indole-6-carboxylate.

A) Methyl 3-[4-(aminomethyl)phenyl]-1,9-dimethyl-2-oxo-2,9-dihydro-1H-pyrido[2,3-b]indole-6-carboxylate.

A mixture of 1 g of the compound from Preparation 3.22, 0.3 g of Raney® nickel and 5 ml of concentrated NaOH in 50 ml of MeOH is hydrogenated at 30° C. under a pressure of 50 bars. The catalyst is filtered off and the filtrate is brought to a pH of 7 by addition of concentrated HCl and concentrated under vacuum. The residue is taken up in water and the precipitate formed is filtered off with suction and dried. The product obtained is taken up in 10 ml of MeOH, admixed dropwise with 0.565 g of thionyl chloride and left with stirring at AT for 2 hours. It is concentrated under vacuum and dried and the compound expected is used as it is.

B) Methyl 3-[4-[[bis(4-methoxybenzyl)amino]methyl]phenyl]-1,9-dimethyl-2-oxo-2,9-dihydro-1H-pyrido[2,3-b]indole-6-carboxylate.

A mixture of the compound obtained in the preceding step, 1.48 g of K$_2$CO$_3$ and 0.841 g of 4-methoxybenzyl chloride in 10 ml of DMF is heated at 80° C. for 18 hours: The reaction mixture is poured into water and the precipitate formed is filtered off with suction and dried. This gives 0.5 g of the expected compound.

Preparation 3.30

Methyl 1,9-dimethyl-3-[4-(morpholin-4-yl-methyl)phenyl]-2-oxo-2,9-dihydro-1H-pyrido[2,3-b]indole-6-carboxylate.

A) Methyl 3-(4-formylphenyl)-1,9-dimethyl-2-oxo-2,9-dihydro-1H-pyrido[2,3-b]indole-6-carboxylate.

A mixture of 1.87 g of the compound from Preparation 3.22, 7.53 g of sodium hypophosphite and 7 g of Raney® nickel in 190 ml of a pyridine/AcOH/water mixture (30/10/6; v/v/v) is heated at 65° C. for 18 hours. The catalyst is filtered off with suction and the filtrate is concentrated under vacuum. The residue is taken up in water and the precipitate formed is filtered off with suction and dried. This gives 1.6 g of the expected compound, m.p.=230° C.

B) Methyl 1,9-dimethyl-3-(4-(morpholin-4-ylmethyl)phenyl]-2-oxo-2,9-dihydro-1H-pyrido[2,3-b]indole-6-carboxylate.

A mixture of 0.374 g of the compound obtained in the preceding step, 0.174 ml of morpholine and 0.255 g of sodium triacetoxyborohydride in 5 ml of DMF is admixed with 1 g of 4 Å zeolites and left with stirring at AT for 18 hours. The reaction mixture is filtered and the filtrate is concentrated under vacuum. The residue is taken up in water and the precipitate formed is filtered off with suction, washed with EtOH and dried. This gives 0.29 g of the expected compound, m.p.=175° C.

Preparation 3.31

6-Acetyl-3-(2,4-dichlorophenyl)-1,9-dimethyl-1,9-dihydro-2H-pyrido[2,3-b]indol-2-one.

A) 3-(2,4-Dichlorophenyl)-1,9-dimethyl-1,9-dihydro-2H-pyrido[2,3-b]indol-2-one.

This compound is prepared according to the procedures described in WO 2004/041817, compound 28, m.p.=241° C.

B) 6-Acetyl-3-(2,4-dichlorophenyl)-1,9-dimethyl-1,9-dihydro-2H-pyrido[2,3-b]indol-2-one.

A solution of 0.5 g of the compound obtained in the preceding step in 20 ml of anhydrous DCM is cooled to 0° C., 0.75 g of aluminium chloride and 0.2 ml of acetyl chloride are added and the mixture is left with stirring at AT for 3 hours. The reaction mixture is poured onto ice and extracted with DCM, the organic phase is washed with saturated NaCl solution and dried over $Na_2SO_4$ and the solvent is evaporated under vacuum. This gives 0.6 g of the expected compound.

$^1$H NMR: DMSO-$d_6$ (300 MHz) : δ (ppm) : 2.63: s: 3H; 4.02: s: 3H; 4.20: s: 3H; 7.43-7.50: m: 2H; 7.69-7.73: m: 2H; 7.89: dd: 1H; 8.38: s: 1H; 8.62: s: 1H.

Preparation 3.32

1,9-Dimethyl-2-oxo-3-phenyl-2,9-dihydro-1H-pyrido[2,3-b]indole-6-carbohydrazide.

A) 1,9-Dimethyl-2-oxo-3-phenyl-2,9-dihydro-1H-pyrido[2,3-b]indole-6-carboxylic acid.

A solution of 1.6 g of the compound from Preparation 3.7 in 75 ml of MeOH and 18 ml of water is admixed with 0.8 g of LiOH, $H_2O$ and then heated at reflux for 3 hours. The MeOH is concentrated under vacuum, the residue is acidified to a pH of 1 by adding 1N HCl and the precipitate formed is filtered off with suction. The precipitate is taken up in MeOH, the solvent is evaporated under vacuum and the residue is triturated in a PE/AcOEt mixture (90/10; v/v) and filtered off with suction. This gives 1.5 g of the expected compound.

$^1$H NMR: DMSO-$d_6$ (300 MHz): δ (ppm) : 4.01: s: 3H; 4.16: s: 3H; 7.28-7.42: m: 3H; 7.62: d: 1H; 7.77-7.80: m: 2H; 7.89: dd: 1H; 8.50-8.57: m: 2H.

B) tert-Butyl 2-[[1,9-dimethyl-2-oxo-2,9-dihydro-1H-pyrido[2,3-b]indol-6-yl]carbonyl]hydrazinecarboxylate.

A solution of 1.5 g of the compound obtained in the preceding step in 40 ml of DCM and 10 ml of DMF is admixed with 0.66 g of tert-butyl hydrazinecarboxylate, 2.5 g of PyBOP and 0.9 ml of DIPEA and then left with stirring at AT for 4 hours. The reaction mixture is poured into saturated $NH_4Cl$ solution and extracted with DCM, the organic phase is dried over $MgSO_4$ and the solvent is evaporated under vacuum. The residue is chromatographed on silica gel, eluting with AcOEt and then with an AcOEt/MeOH mixture (95/5; v/v). The product obtained is taken up in an AcOEt/cyclohexane mixture (75/25; v/v) and the precipitate formed is filtered off with suction. This gives 1.9 g of the expected compound.

$^1$H NMR: DMSO-$d_6$ (300 MHz): δ (ppm): 1.39: s: 9H; 4.06: s: 3H; 4.17: s: 3H; 7.29-7.42: m: 3H; 7.67: d: 1H; 7.76-7.82: m: 3H; 8.40: s: 1H; 8.51: s: 1H; 8.91: s: 1H; 10.11: s: 1H.

C) 1,9-Dimethyl-2-oxo-3-phenyl-2,9-dihydro-1H-pyrido[2,3-b]indole-6-carbohydrazide.

A mixture of 1.9 g of the compound obtained in the preceding step in 100 ml of MeOH and 10 ml of 6N HCl is heated at 80° C. for 2 hours. The reaction mixture is concentrated under vacuum and the residue is taken up in MeOH, brought to a pH of 7 by adding triethylamine and concentrated under vacuum. The residue is chromatographed on silica gel, eluting with AcOEt and then with an AcOEt/MeOH/28% $NH_4OH$ mixture (90/10/1; v/v/v). This gives the expected compound.

$^1$H NMR: DMSO-$d_6$ (300 MHz): δ (ppm): 4.00: s: 3H; 4.14: s: 3H; 7.26-7.76: m: 7H; 8.39: s: 1H; 8.47: s: 1H; 9.68: s: 1H.

Preparation 3.33

3-(2,4-Dichlorophenyl)-1,9-dimethyl-2-oxo-2,9-dihydro-1H-pyrido[2,3-b]indole-6-carbohydrazide.

A) tert-Butyl 2-[[3-(2,4-dichlorophenyl)-1,9-dimethyl-2-oxo-2,9-dihydro-1H-pyrido[2,3-b)indol-6-yl]-carbonyl)hydrazinecarboxylate.

This compound is prepared according to the procedure described in step B in Preparation 3.32, starting from the compound obtained in step A of the variant of Example 5. This gives 0.33 g of the expected compound.

$^1$H NMR: DMSO-$d_6$ (300 MHz): δ (ppm): 1.44: s: 9H; 4.03: s: 3H; 4.26: s: 3H; 7.43-7.50: m: 2H; 7.68-7.72: m: 2H; 7.80-7.82: m: 1H; 8.23: s: 1H; 8.43: s: 1H; 8.86: s: 1H; 10.08: s: 1H.

B) 3-(2,4-Dichlorophenyl)-1,9-dimethyl-2-oxo-2,9-dihydro-1H-pyrido[2,3-b]indole-6-carbohydrazide.

This compound is prepared according to the procedure described in step C of Preparation 3.32, starting from the compound from the preceding step.

$^1$H NMR: DMSO-$d_6$ (300 MHz) δ (ppm): 4.02: s: 3H; 4.18: s: 3H; 7.42-7.50: m: 2H; 7.65-7.79: m: 3H; 8.21: s: 1H; 8.38: d: 1H; 9.64: s: 1H.

Preparation 3.34

3-(2,4-Dimethoxyphenyl)-1-methyl-2-oxo-2,9-dihydro-1H-pyrido[2,3-b]indole-6-carbohydrazide.

A) 3-(2,4-Dimethoxyphenyl)-1-methyl-2-oxo-2,9-dihydro-1H-pyrido[2,3-b]indole-6-carboxylic acid.

A suspension of 0.9 g of the compound obtained in step B of Preparation 3.1 in 6 ml of water is admixed with 2 g of KOH and then 0.5 ml of 35% $H_2O_2$ and the suspension is heated at 130° C. for 2 days. After cooling to AT, it is alkalified by adding concentrated NaOH, and the aqueous phase is washed with AcOEt and acidified by adding 1N HCl. The precipitate formed is filtered off with suction and washed with water. The precipitate is taken up in MeOH and the solvent is evaporated under vacuum. The precipitate is taken up in a propan-2-ol/PE mixture (50/50; v/v) and triturated and the precipitate is filtered off with suction. This gives 0.9 g of the expected compound.

$^1$H NMR: DMSO-d$_6$ (300 MHz): δ (ppm): 3.69-3.80: m: 9H; 6.53-6.61: m: 2H; 7.20: d: 1H; 7.35: d: 1H; 7.80: d: 1H; 7.94: s: 1H; 8.30: s: 1H.

B) tert-Butyl 2-[[3-(2,4-dimethoxyphenyl)-1-methyl-2-oxo-2,9-dihydro-1H-pyrido[2,3-b]indol-6-yl]carbonyl]-hydrazinecarboxylate.

This compound is prepared according to the procedure described in step B of Preparation 3.32, starting from the compound from the preceding step.

$^1$H NMR: DMSO-d$_6$ (300 MHz): δ (ppm): 1.43: s: 9H; 3.68: s: 3H; 3.71: s: 3H; 3.81: s: 3H; 6.54-6.63: m: 2H; 7.18: d: 1H; 7.51: d: 1H; 7.69-7.74: m: 1H; 7.98: s: 1H; 8.27: s: 1H; 8.84: se: 1H; 10.00: se: 1H; 12.23: se: 1H.

C) 3-(2,4-Dimethoxyphenyl)-1-methyl-2-oxo-2,9-dihydro-1H-pyrido[2,3-b]indole-6-carbohydrazide.

A mixture of 0.39 g of the compound obtained in the preceding step in 15 ml of MeOH and 1 ml of 6N HCl is left with stirring at AT overnight. The reaction mixture is concentrated under vacuum and the residue is taken up in triethylamine and pyridine until it dissolves, and chromatographed on silica gel, eluting with an AcOEt/MeOH/28% NH$_4$OH mixture (90/10/1; v/v/v). This gives 0.2 g of the expected compound.

Preparation 3.35

3-(2,4-Dichlorophenyl)-N'-hydroxy-1,9-dimethyl-2-oxo-2,9-dihydro-1H-pyrido[2,3-b]indole-6-carboximidamide.

A suspension of 1 g of the compound from Preparation 3.27 step A in 20 ml of anhydrous EtOH is admixed with 0.91 g of hydroxylamine hydrochloride and 1.82 ml of triethylamine and heated at reflux for 3 days. After cooling to AT, the reaction mixture is admixed with MeOH and pyridine and chromatographed on silica gel, eluting with an AcOEt/MeOH/triethylamine mixture (90/10/2; v/v/v). The product obtained is taken up in water and triturated and the precipitate formed is filtered off with suction and washed with a propan-2-ol/PE mixture (50/50; v/v). This gives 0.7 g of the expected compound.

$^1$H NMR: DMSO-d$_6$ (300 MHz): δ (ppm): 4.02: s: 3H; 4.20: s: 3H; 7.41-7.50: m: 2H; 7.65-7.68: m: 2H; 7.82: d: 1H; 8.30: s: 1H; 8.41: s: 1H.

Preparations of Compounds of Formula (V).

Preparation 4.1

N''-Hydroxy-N,N-bis(4-methoxybenzyl)guanidine (V).

A) Bis(4-methoxybenzyl)cyanamide.

A solution of 1 g of cyanamide in 50 ml of DMF is admixed with 13.1 g of K$_2$CO$_3$ and 6.5 ml of 4-methoxybenzyl chloride and then heated at 80° C. for 20 hours. After cooling to AT, the reaction mixture is poured into water, and extracted with AcOEt, the organic phase is dried over MgSO$_4$ and the solvent is evaporated under vacuum. The residue is chromatographed on silica gel, eluting with an AcOEt/cyclohexane mixture (75/25; v/v). This gives 6.5 g of the expected compound in the form of an oil.

NMR CDCl$_3$ (300 MHz): δ (ppm): 3.73: s: 6H; 3.95: s: 4H; 6.82: d: 4H; 7.16: d: 4H.

B) N''-Hydroxy-N,N-bis(4-methoxybenzyl)guanidine (V).

A solution of 6.5 g of the compound obtained in the preceding step in 40 ml of EtOH is admixed with 3.2 g of hydroxylamine hydrochloride and 6.4 ml of triethylamine and then left with stirring at AT for 5 hours. The reaction mixture is concentrated under vacuum, the residue is taken up in water, extracted with AcOEt and dried over MgSO$_4$ and the solvent is evaporated under vacuum. This gives 3.6 g of the expected compound.

NMR CDCl$_3$ (300 MHz): δ (ppm): 3.80: s: 6H; 4.24: s: 4H; 6.84: d: 4H; 7.16: d: 4H.

Preparation 4.2

N'-Hydroxy-2-phenoxyethanimidamide.

A mixture of 1 g of phenoxyacetonitrile, 2.4 g of K$_2$CO$_3$ and 1.2 g of hydroxylamine hydrochloride in 60 ml of EtOH and 10 ml of water is heated at reflux for 3 hours. The reaction mixture is concentrated under vacuum and the residue is taken up in water and extracted with AcOEt. The organic phase is extracted with 1N HCl solution, the aqueous phase is alkalified by adding 1N NaOH solution, extracted with AcOEt and dried over MgSO$_4$, and the solvent is evaporated under vacuum. This gives 0.9 g of the expected compound in the form of a colourless oil which crystallizes.

$^1$H NMR: CDCl$_3$ (300 MHz): δ (ppm): 4.56: s: 2H; 4.90: s: 2H; 6.95-7.02: m: 3H; 7.26-7.32: m: 2H.

EXAMPLE 1

Compound 7

3-(2,4-Dimethoxyphenyl)-1-methyl-2-oxo-2,9-dihydro-1H-pyrido[2,3-b]indole-6-carbaldehyde O-ethyloxime.

0.3 g of the compound from Preparation 3.1 is dissolved in 20 ml of ethanol; 0.4 g of O-ethylhydroxylamine hydrochloride dissolved in 1 ml of water is added and the mixture is left with stirring at AT for 2 hours. The ethanol is evaporated and the residue is taken up in water and then extracted with AcOEt. It is chromatographed on silica, eluting with AcOEt and then with AcOEt/MeOH (98/2; v/v). This gives 70 mg of the expected compound.

$^1$H NMR: DMSO (300 MHz): 1.26 ppm: t: 3H; 3.66 ppm: s: 3H; 3.70 ppm: s: 3H; 3.80 ppm: s: 3H; 4.13 ppm: q: 2H; 6.52-6.56 ppm: dd: 1H; 6.60 ppm: d: 1H; 7.16 ppm: d: 1H; 7.48 ppm: s: 2H; 8 ppm: s: 2H; 8.26 ppm: s: 1H; 12.14 ppm: s: 1H.

EXAMPLE 2

Compound 8

3-(2,4-Dimethoxyphenyl)-1-methyl-6-(3-phenyl-1-[1,2,4]oxadiazol-5-yl)-1,9-dihydro-2H-pyrido[2,3-b]indol-2-one.

0.5 g of the compound from Preparation 3.2, step A is dissolved in 10 ml of DMF; 0.29 g of CDI is added, and then the mixture is stirred at AT for 30 minutes. 0.22 g of N'-hydroxybenzenecarboximidamide dissolved in 4 ml of DMF is added, the mixture is stirred at AT for 6 hours, and then 0.26 g of CDI is added and the mixture is heated at 115° C. for 18 hours. Water is added, extraction is carried out with ether, followed by drying over MgSO$_4$ and chromatography on silica, eluting with AcOEt and then with AcOEt/MeOH (98/2; v/v). The residue obtained is triturated in an AcOEt/cyclohexane mixture (50/50; v/v) and then filtered. This gives 0.15 g of the expected compound.

$^1$H NMR: DMSO (300 MHz): 3.69 ppm: s: 3H; 3.72 ppm: s: 3H; 3.81 ppm: s: 3H; 6.55-6.59 ppm: dd: 1H; 6.63 ppm: d: 1H; 7.18 ppm: d: 1H; 7.55-7.62 ppm: m: 3H; 7.68 ppm: d: 1H;

8.01-8.05 ppm: dd: 1H; 8.10-8.16 ppm: m: 2H; 8.25 ppm: s: 1H; 8.73 ppm: d: 1H; 12.48 ppm: s: 1H.

EXAMPLE 3

Compound 3

3-(2,4-Dichlorophenyl)-1-methyl-6-(3-methyl-[1,2,4] oxadiazol-5-yl)-1,9-dihydro-2H-pyrido[2,3-b]indol-2-one.

0.12 g of 60% NaH is suspended in 12 ml of anhydrous THF; 0.32 g of molecular sieve and then 0.22 g of N-hydroxyethanimidamide are added and then the mixture is heated at 70° C. for one and a half hours. 0.4 g of the compound from Preparation 3.5 is added and then the mixture is heated at 80° C. for 2 hours. Water is added and extraction is carried out with AcOEt, followed by chromatography on silica, eluting with AcOEt/cyclohexane (60/40; v/v) and then with pure AcOEt. This gives 120 mg of the expected compound.

1H NMR: DMSO (300 MHz): 2.47 ppm: s: 3H; 3.77 ppm: s: 3H; 7.49-7.56 ppm: m: 2H; 7.71-7.75 ppm: m: 2H; 8.01 ppm: d: 1H; 8.45 ppm: s: 1H; 8.73 ppm: s: 1H; 12.64 ppm: s: 1H.

EXAMPLE 4

Compound 2

3-(2,4-Dichlorophenyl)-1,9-dimethyl-6-(3-methyl-[1,2,4] oxadiazol-5-yl)-1,9-dihydro-2H-pyrido[2,3-b]indol-2-one.

7 mg of 60% NaH are suspended in 2 ml of DMF, and 50 mg of the compound from Example 3 and then 0.02 ml of CH₃I are added, and then the mixture is left with stirring at AT for 2 hours. The reaction mixture is poured into water and then the precipitate formed is filtered off. It is washed with water and then with an AcOEt/cyclohexane mixture (50/50; v/v), to give 30 mg of the expected compound.

¹H NMR: DMSO (300 MHz): 2.27 ppm: s: 3H; 4.03 ppm: s: 3H; 4.22 ppm: s: 3H; 7.43-7.50 ppm: m: 2H; 7.69 ppm: s: 1H; 7.84 ppm: d: 1H; 7.98 ppm: d: 1H; 8.44 ppm: s: 1H; 8.69 ppm: s: 1H.

EXAMPLE 5

Compound 14

6-(3-Amino-1,2,4-oxadiazol-5-yl)-3-(2,4-dichlorophenyl)-1,9-dimethyl-1,9-dihydro-2H-pyrido[2,3-b]indol-2-one.

A mixture of 3 g of molecular sieve in 15 ml of ethanol is admixed with 0.26 g of sodium and left with stirring at AT for 15 minutes. Subsequently 0.9 g of N''-hydroxyguanidine hemisulphate hemihydrate is added and the mixture is left with stirring at AT for 1 hour. Finally, 0.4 g of the compound obtained in Preparation 3.26 is added and the mixture is heated at reflux for 4 days. After cooling to AT, the reaction mixture is admixed with water and extracted with AcOEt, the organic phase is dried over MgSO₄ and the solvent is evaporated under vacuum. The residue is chromatographed on silica gel, eluting with an AcOEt/cyclohexane mixture (75/25; v/v). This gives 0.02 g of the expected product.

¹H NMR: DMSO-d₆ (300 MHz): δ (ppm): 4.04: s: 3H; 4.22: s: 3H; 6.32: s: 2H; 7.43-7.51: m: 2H; 7.70: d: 1H; 7.81: d: 1H; 7.90: dd: 1H; 8.42: s: 1H; 8.5: d: 1H.

It is also possible to prepare compound 14 by following the procedures described in steps A, B, C and D below.

A) 3-(2,4-Dichlorophenyl)-1,9-dimethyl-2-oxo-2,9-dihydro-1H-pyrido[2,3-b]indole-6-carboxylic acid.

A mixture of 9.5 g of the compound obtained in Preparation 3.26 in 100 ml of MeOH is admixed with a solution of 5.14 g of KOH as pellets in 90 ml of water and heated at reflux for 18 hours. After cooling to AT and then with an ice bath, the reaction mixture is acidified to a pH of 1 by adding 5N HCl solution, diluting with water to allow stirring. The precipitate formed is filtered off with suction, washed with water and dried. This gives 9.1 g of the expected compound.

B) 3-(2,4-Dichlorophenyl)-1,9-dimethyl-2-oxo-2,9-dihydro-1H-pyrido[2,3-b]indole-6-carbonyl chloride.

A suspension of 9.1 g of the compound obtained in the preceding step in 100 ml of anhydrous THF is cooled with an ice bath, admixed dropwise with a solution of 45 ml of thionyl chloride in 45 ml of THF and left with stirring for 15 minutes before being concentrated at AT under vacuum. The residue is taken up in 40 ml of DCM and the solvent is evaporated under vacuum. This gives the expected compound, which is used as it is.

C) N-Cyano-3-(2,4-dichlorophenyl)-1,9-dimethyl-2-oxo-2,9-dihydro-1H-pyrido[2,3-b]indole-6-carboxamide.

A solution of the compound obtained in the preceding step in 100 ml of anhydrous THF is admixed with a solution of 10 g of cyanamide in 50 ml of THF and heated at 60° C. under an argon atmosphere. After 30 minutes, 100 ml of THF are added and the resulting suspension is concentrated under vacuum. The residue is taken up in 200 ml of EtOH and left with stirring at AT overnight and the precipitate formed is filtered off with suction, washed with EtOH and dried under vacuum. The product obtained is taken up in water and the precipitate is filtered off with suction and dried. This gives 8.3 g of the expected compound.

D) 6-(3-Amino-1,2,4-oxadiazol-5-yl)-3-(2,4-dichlorophenyl)-1,9-dimethyl-1,9-dihydro-2H-pyrido[2,3-b]indol-2-one.

A mixture of 3 g of the compound obtained in the preceding step and 0.9 g of hydroxylamine hydrochloride in 60 ml of pyridine is heated at 120° C. for 15 minutes. Subsequently 30 g of basic alumina 60 are added and the mixture is concentrated to dryness under vacuum. The residue is chromatographed on basic alumina 60, eluting with AcOEt and then with a gradient of the mixture AcOEt/MeOH (to 97/3; v/v). This gives 1.2 g of the expected compound.

EXAMPLE 6

Compound 20

3-(2,4-Dichlorophenyl)-1,9-dimethyl-2-oxo-2,9-dihydro-1H-pyrido[2,3-b]indole-6-carbaldehyde oxime.

A solution of 0.2 g of the compound obtained in Preparation 3.27 in 15 ml of 96% EtOH is admixed with 0.18 g of hydroxylamine hydrochloride and left with stirring at AT for 3 hours. The solvent is concentrated under vacuum, the residue is taken up in water and the precipitate formed is filtered off with suction. The precipitate is dissolved in an MeOH/pyridine mixture and this solution is chromatographed on silica gel, eluting with a DCM/MeOH mixture (98/2; v/v). This gives 0.14 g of the expected compound, m.p.=287-290° C.

¹H NMR: DMSO-d₆ (300 MHz) : δ (ppm): 4.01: s: 3H; 4.17: s: 3H; 5.76: s: 1H; 7.42-7.49: m: 2H; 7.53-7.57: dd: 1H; 7.63-7.69: m: 2H; 8.06: d: 1H; 8.19-8.23: m: 2H.

EXAMPLE 7

Compound 21

3-(2,4-Dichlorophenyl)-1,9-dimethyl-2-oxo-2,9-dihydro-1H-pyrido[2,3-b]indole-6-carbaldehyde O-ethyloxime.

A solution of 0.2 g of the compound obtained in Preparation 3.27 in 15 ml of EtOH is admixed with 0.25 g of O-ethylhydroxylamine hydrochloride and left with stirring at AT for 20 hours. The reaction mixture is concentrated under vacuum, the residue is taken up in water and the precipitate formed is filtered off with suction. The precipitate is taken up in an AcOEt/MeOH mixture (50/50; v/v) and this solution is chromatographed on silica gel, eluting with an AcOEt/cyclohexane mixture (75/25; v/v). The product obtained is taken up in an AcOEt/cyclohexane mixture (50/50; v/v) and the precipitate formed is filtered off with suction. This gives 0.1 g of the expected compound.

$^1$H NMR: DMSO-d$_6$ (300 MHz): δ (ppm): 1.27: t: 3H; 4.02: s: 3H; 4.12-4.22: m: 5H; 7.42-8.48: m: 8H.

EXAMPLE 8

Compound 22

3-(2,4-Dichlorophenyl)-1,9-dimethyl-2-oxo-2,9-dihydro-1H-pyrido[2,3-b]indole-6-carbaldehyde O-isobutyloxime.

A solution of 0.14 g of compound 20 in 4 ml of DMF is admixed with 0.017 g of 60% sodium hydride in oil and left with stirring at AT for 10 minutes. Subsequently 0.076 ml of isobutyl bromide is added and the mixture is left with stirring at AT overnight. The reaction mixture is poured into saturated NH$_4$Cl solution and extracted with AcOEt, the organic phase is dried over MgSO$_4$ and the solvent is evaporated under vacuum. The residue is chromatographed on silica gel, eluting with an AcOEt/cyclohexane mixture (75/25; v/v). This gives 0.035 g of the expected compound, m.p.=100-110° C.

$^1$H NMR: DMSO-d$_6$ (300 MHz): δ (ppm): 0.92: s: 3H; 0.94: s: 3H; 2.02: m: 1H; 3.88: d: 2H; 4.01: s: 3H; 4.17: s: 3H; 7.42-7.50: m: 2H; 7.54-7.57: dd: 1H; 7.65-7.69: m: 2H; 8.10: d: 1H; 8.26: s: 1H; 8.30: s: 1H.

EXAMPLE 9

Compound 23

[[[[3-(2,4-Dichlorophenyl)-1,9-dimethyl-2-oxo-2,9-dihydro-1H-pyrido[2,3-b]indol-6-yl]methylene]amino]oxy]acetic acid.

A solution of 0.3 g of the compound obtained in Preparation 3.27 in 25 ml of 96% EtOH is admixed with 0.426 g of O-(carboxymethyl)hydroxylamine hemihydrochloride and left with stirring at AT overnight. The reaction mixture is concentrated under vacuum, the residue is taken up in water and triturated and the precipitate formed is filtered off with suction. The precipitate is taken up in 2N NaOH solution, the aqueous phase is washed with AcOEt and acidified to a pH of 1 by adding 6N HCl solution, the precipitate formed is filtered off with suction and the filtrate is extracted with AcOEt. The precipitate and the organic phase are combined and the solvent is evaporated under vacuum. The residue is taken up in hot propan-2-ol and the precipitate formed is filtered off hot with suction and washed with ether. This gives 0.135 g of the expected compound.

$^1$H NMR: DMSO-d$_6$ (300 MHz): δ (ppm): 4.01: s: 3H; 4.18: s: 3H; 4.64: s: 2H; 7.42-7.49: m: 2H; 7.55: dd: 1H; 7.67-7.69: m: 2H; 8.12: d: 1H; 8.27: s: 1H; 8.37: s: 1H; 12.8: se: 1H.

EXAMPLE 10

Compound 26

6-(3-Amino-1,2,4-oxodiazol-5-yl)-3-(2,4-dimethoxyphenyl)-1,9-dimethyl-1,9-dihydro-2H-pyrido[2,3-b]indol-2-one.

A) 6-[3-[Bis(4-methoxybenzyl)amino]-1,2,4-oxodiazol-5-yl]-3-(2,4-dimethoxyphenyl)-1,9-dimethyl-1,9-dihydro-2H-pyrido[2,3-b]indol-2-one.

A mixture of 6.3 g of molecular sieve in 63 ml of anhydrous EtOH is admixed with 0.78 g of sodium and then, following dissolution, 5.6 g of the compound obtained in Preparation 4.1 are added and the mixture is left with stirring at AT and under an argon atmosphere for 2 hours. Subsequently 1.2 g of the compound obtained in Preparation 3.28 are added and the mixture is heated at reflux overnight. After cooling to AT, the reaction mixture is admixed with DCM and AcOEt, the molecular sieve is filtered off and washed with DCM, the filtrate is washed with 1N HCl solution and with 2N NaOH solution, the organic phase is dried over MgSO$_4$ and the solvent is evaporated under vacuum. The residue is chromatographed on silica gel, eluting with a DCM/MeOH mixture (97/3; v/v). The product obtained is taken up in MeOH and triturated and the precipitate formed is filtered off with suction, washed with MeOH and dried under vacuum. This gives 0.596 g of the expected compound.

$^1$H NMR: DMSO-d$_6$ (300 MHz): δ (ppm): 3.71: m: 9H; 3.79: s: 3H; 3.99: s: 3H; 4.20: s: 3H; 4.48: s: 4H; 6.56: m: 1H; 6.61: s: 1H; 6.90: d: 4H; 7.14: d: 1H; 7.23: d: 4H; 7.79: d: 1H; 7.91: d: 1H; 8.24: s: 1H; 8.59: s: 1H.

B) 6-(3-Amino-1,2,4-oxodiazol-5-yl)-3-(2,4-dimethoxyphenyl)-1,9-dimethyl-1,9-dihydro-2H-pyrido[2,3-b]indol-2-one.

A solution of 0.593 g of the compound obtained in the preceding step in 10 ml of DCM and 2 ml of water is admixed with 1 g of DDQ and heated at reflux overnight. After cooling to AT, the precipitate formed is filtered off with suction and washed with DCM and then with water. The precipitate is dissolved in MeOH and the solution is chromatographed on silica gel, eluting with AcOEt and then with an AcOEt/MeOH mixture (90/10; v/v). The product obtained is taken up in MeOH and the precipitate formed is filtered off with suction and washed with MeOH. This gives 0.094 g of the expected compound, m.p.=320-322° C.

$^1$H NMR: DMSO-d$_6$ (300 MHz): δ (ppm): 3.76: s: 3H; 3.86: s: 3H; 4.05: s: 3H; 4.25: s: 3H; 6.39: s: 2H; 6.62: dd: 1H; 6.68: d: 1H; 7.22: d: 1H; 7.84: d: 1H; 7.93: dd: 1H; 8.26: s: 1H; 8.57: s: 1H.

EXAMPLE 11:

Compound 39

3-[4-(Aminomethyl)phenyl]-6-(3-amino-1,2,4-oxadiazol-5-yl)-1,9-dimethyl-1,9-dihydro-2H-pyrido[2,3-b]indol-2-one.

A) 3-[4-[[Bis(4-methoxybenzyl)amino]methyl]phenyl]-6-[3-[bis(4-methoxybenzyl)amino]-1,2,4-oxadiazol-5-yl]-1,9-dimethyl-1,9-dihydro-2H-pyrido[2,3-b]indol-2-one.

This compound is prepared according to the procedure described in step A of Example 10, starting from the compound from Preparation 3.29 and from the compound from Preparation 4.1.

B) 3-[4-(Aminomethyl)phenyl]-6-(3-amino-1,2,4-oxadiazol-5-yl)-1,9-dimethyl-1,9-dihydro-2H-pyrido[2,3-b]indol-2-one.

This compound is prepared according to the procedure described in step B of Example 10. This gives 0.2 g of the expected compound.

$^1$H NMR: DMSO-$d_6$/TFA (200 MHz): δ (ppm): 3.9: s: 2H; 4.0: s: 3H; 4.2: s: 3H; 7.5: d: 2H; 7.8-8.0: m: 4H; 8.65: d: 2H.

EXAMPLE 12

Compound 41

3-(2,4-Dichlorophenyl)-6-[3-(dimethylamino)-1,2,4-oxadiazol-5-yl]-1,9-dimethyl-1,9-dihydro-2H-pyrido[2,3-b]indol-2-one.

A solution of 0.09 g of compound 14 in 3 ml of DMF is admixed with 0.025 g of 60% sodium hydride in oil and then with 0.04 ml of methyl iodide and the mixture is left with stirring at AT for 2 hours. Water is added to the reaction mixture and the precipitate formed is filtered off with suction and washed with water and then with a propan-2-ol/PE mixture (50/50; v/v). This gives 0.07 g of the expected compound, m.p.=320-324° C.

$^1$H NMR: pyridine-$d_5$ (300 MHz): δ (ppm): 2.94: s: 6H; 3.80: s: 3H; 3.82: s: 3H; 7.32: dd: 1H; 7.47-7.52: m: 2H; 7.58: d: 1H; 7.95: s: 1H; 8.09: dd: 1H; 8.66: d: 1H.

EXAMPLE 13

Compound 42

N-[5-[3-(2,4-Dichlorophenyl)-1,9-dimethyl-2-oxo-2,9-dihydro-1H-pyrido[2,3-b]indol-6-yl]-1,2,4-oxadiazol-3-yl] cyclopropanecarboxamide.

A solution of 0.1 g of compound 14 in 5 ml of pyridine is admixed with 0.4 ml of cyclopropanecarbonyl chloride and the mixture is heated at 50° C. for 2 hours. After cooling to AT it is extracted with AcOEt, the organic phase is washed with water and dried over Na$_2$SO$_4$ and the solvent is evaporated under vacuum. The residue is chromatographed on silica gel, eluting with an AcOEt/MeOH mixture (90/10; v/v). The product obtained is taken up in an AcOEt/cyclohexane mixture (50/50; v/v) and triturated and the precipitate formed is filtered off with suction. This gives 0.065 g of the expected compound, m.p.=292-295° C.

$^1$H NMR: DMSO-$d_6$ (300 MHz): δ (ppm): 0.86: m: 4H; 1.99: m: 1H; 4.03: s: 3H; 4.23: s: 3H; 7.43-7.51: m: 2H; 7.70: s: 1H; 7.86: d: 1H; 7.96: dd: 1H; 8.45: s: 1H; 8.66: s: 1H; 11.48: s: 1H.

EXAMPLE 14

Compound 44

N-[5-[3-(2,4-Dichlorophenyl)-1,9-dimethyl-2-oxo-2,9-dihydro-1H-pyrido[2,3-b]indol-6-yl]-1,2,4-oxadiazol-3-yl] methanesulphonamide.

A solution of 0.1 g of compound 14 in 10 ml of pyridine and 1 ml of DCM is admixed with 0.08 ml of methanesulphonyl chloride and 0.025 g of DMAP and then the mixture is left with stirring at AT for 96 hours. The reaction mixture is poured into water and extracted with AcOEt, the organic phase is washed with saturated NaCl solution and dried over Na$_2$SO$_4$ and the solvent is evaporated under vacuum. The residue is chromatographed on silica gel, eluting with a DCM/MeOH mixture (95/5; v/v). This gives 0.025 g of the expected compound, m.p.=263-266° C.

$^1$H NMR: DMSO-$d_6$ (300 MHz): δ (ppm): 3.22: s: 3H; 4.03: s: 3H; 4.23: s: 3H; 7.43-7.51: m: 2H; 7.69: d: 1H; 7.84: d: 1H; 7.95: d: 1H; 8.47: s: 1H; 8.64: s: 1H; 11.82: s: 1H.

EXAMPLE 15

Compound 49

[3-(2,4-Dichlorophenyl)-1-methyl-6-(3-methyl-1,2,4-oxadiazol-5-yl)-2-oxo-1,2-dihydro-9H-pyrido[2,3-b]indol-9-yl]acetonitrile.

A mixture of 0.3 g of compound 3, 0.195 g of K$_2$CO$_3$ and 0.1 ml of bromoacetonitrile in 20 ml of DMF is heated at 80° C. for 4 days. After cooling to AT, the reaction mixture is poured into saturated NH$_4$Cl solution and extracted with AcOEt, the organic phase is washed with saturated NaCl solution and dried over MgSO$_4$ and the solvent is evaporated under vacuum. The residue is chromatographed on silica gel, eluting with an AcOEt/cyclohexane mixture (75/25; v/v). The product obtained is triturated in cyclohexane and the precipitate formed is filtered off with suction. This gives 0.09 g of the obtained compound.

$^1$H NMR: DMSO-$d_6$ (300 MHz): δ (ppm): 2.43: s: 3H; 4.02: s: 3H; 6.01: s: 2H; 7.45-7.53: m: 2H; 7.71: d: 1H; 8.00: d: 1H; 8.09: dd: 1H; 8.52: s: 1H; 8.76: d: 1H.

EXAMPLE 16

Compound 50

3-(2,4-Dichlorophenyl)-1-methyl-6-(3-methyl-1,2,4-oxadiazol-5-yl)-9-(2-morpholin-4-ylethyl)-1,9-dihydro-2H-pyrido[2,3-b]indol-2-one.

A mixture of 0.3 g of compound 3, 0.39 g of K$_2$CO$_3$ and 0.263 g of 2-chloroethylmorpholine hydrochloride in 15 ml of DMF is heated at 80° C. for 4 days. After cooling to AT, the reaction mixture is poured into saturated NaCl solution and the precipitate formed is filtered off with suction and washed with water. The precipitate is taken up in MeOH and the solvent is concentrated under vacuum. The residue is triturated in a propan-2-ol/PE mixture (50/50; v/v) and the precipitate formed is filtered off with suction. This gives 0.3 g of the expected compound.

$^1$H NMR: DMSO-$d_6$ (300 MHz): δ (ppm): 2.35-2.42: m: 7H; 2.73: t: 2H; 3.42-3.44: m: 4H; 4.01: s: 3H; 4.75-4.79: m: 2H; 7.43-7.51: m: 2H; 7.69: d: 1H; 7.87: d: 1H; 8.00: dd: 1H; 8.46: s: 1H; 8.70: d: 1H.

EXAMPLE 17

Compound 53

3-(2,4-Dichlorophenyl)-6-(N-hydroxyethanimidoyl)-1,9-dimethyl-1,9-dihydro-2H-pyrido[2,3-b]indol-2-one.

A solution of 0.28 g of the compound from Preparation 3.31 in 30 ml of EtOH is admixed with 0.15 g of hydroxylamine hydrochloride and then with 0.3 g of K$_2$CO$_3$ and the mixture is heated at reflux for 3 hours. After cooling to AT, the reaction mixture is admixed with water and the precipitate formed is filtered off with suction. The precipitate is dissolved in a DCM/MeOH mixture and chromatographed on silica gel, eluting with a DCM/MeOH mixture (98/02; v/v). This gives 0.13 g of the expected compound.

$^1$H NMR: DMSO-$d_6$ (300 MHz): δ (ppm): 2.23: s: 3H; 4.02: s: 3H; 4.17: s: 3H; 7.43-7.50: m: 2H; 7.59-7.70: m: 3H; 8.17: s: 1H; 8.30: s: 1H; 11.06: s: 1H.

EXAMPLE 18

Compound 55

6-(5-Amino-1,3,4-oxadiazol-2-yl)-1,9-dimethyl-3 phenyl-1,9-dihydro-2H-pyrido[2,3-b]indol-2-one.

A solution of 1.5 g of the compound from Preparation 3.32 in 30 ml of anhydrous MeOH is admixed with 0.46 g of cyanogen bromide and the mixture is heated at reflux for 2 hours 30 minutes. The reaction mixture is poured into water and alkalified by adding 28% NH$_4$OH solution and the precipitate formed is filtered off with suction. The precipitate is taken up in an MeOH/AcOEt/pyridine mixture, the insoluble material is filtered off and the filtrate is chromatographed on silica gel, eluting with an AcOEt/MeOH mixture (90/10; v/v). This gives 0.5 g of the expected compound, m.p.=308-309° C.

$^1$H NMR: DMSO-$d_6$ (300 MHz): δ (ppm): 4.03: s: 3H; 4.18: s: 3H; 7.13: s: 2H; 7.29-7.43: m: 3H; 7.72-7.80: m: 4H; 7.40: s: 1H; 8.54: m: 1H.

EXAMPLE 19

Compound 58

3-(2,4-Dichlorophenyl)-1,9-dimethyl-6-(5-methyl-1,3,4-oxadiazol-2-yl)-1,9-dihydro-2H-pyrido[2,3-b]indol-2-one.

A suspension of 0.2 g of the compound obtained in Preparation 3.33 and 2 ml of triethyl orthoacetate is admixed with a catalytic amount of para-toluenesulphonic acid and the suspension is heated at 140° C. overnight. After cooling to AT, the precipitate formed is filtered off with suction and washed with water. The precipitate is taken up in a propan-2-ol/PE mixture (50/50; v/v), triturated and filtered off with suction. This gives 0.13 g of the expected compound, m.p.=311-316° C.

$^1$H NMR: DMSO-$d_6$ (300 MHz): δ (ppm): 2.58: s: 3H; 4.03: s: 3H; 4.22: s: 3H; 7.43-7.51: m: 2H; 7.69: se: 1H; 7.81-7.91: m: 2H; 8.44: s: 1H; 8.55: se: 1H.

EXAMPLE 20

Compound 59

3-(2,4-Dichlorophenyl)-1,9-dimethyl-6-(5-methyl-1,2,4-oxodiazol-3-yl)-1,9-dihydro-2H-pyrido[2,3-b]indol-2-one.

A mixture of 0.4 g of the compound from Preparation 3.35, 10 ml of acetic anhydride and 1 ml of acetic acid is heated at reflux for 2 hours. After cooling to AT, the precipitate formed is filtered off with suction and washed with an AcOEt/MeOH mixture (50/50; v/v). This gives 0.24 g of the expected compound, m.p.=306-307° C.

$^1$H NMR: DMSO-$d_6$ (300 MHz): δ (ppm): 2.67: s: 3H; 4.02: s: 3H; 4.20: s: 3H; 7.43-7.51: m: 2H; 7.69: d: 1H; 7.78: d: 1H; 7.90: dd: 1H; 8.41: s: 1H; 8.55: s: 1H.

EXAMPLE 21

Compound 60

6-(5-Amino-1,2,4-oxodiazol-3-yl)-3-(2,4-dichlorophenyl)-1,9-dimethyl-1,9-dihydro-2H-pyrido[2,3-b]-indol-2-one.

A) 3-(2,4-Dichlorophenyl)-1,9-dimethyl-6-[5-(trichloromethyl)-1,2,4-oxodiazol-3-yl]-1,9-dihydro-2H-pyrido[2,3-b] indol-2-one.

A solution of 0.2 g of the compound from Preparation 3.35 in 5 ml of anhydrous dioxane and 0.6 ml of NMP is admixed with 0.107 ml of trichloroacetyl chloride and then with 0.082 ml of pyridine and is left with stirring at AT for 1 hour. The reaction mixture is poured into water and the precipitate formed is filtered off with suction and washed with water and then with toluene and with ether. This gives 0.19 g of the expected compound.

B) 6-(5-Amino-1,2,4-oxodiazol-3-yl)-3-(2,4-dichlorophenyl)-1,9-dimethyl-1,9-dihydro-2H-pyrido[2,3-b]indol-2-one.

5 ml of anhydrous THF are cooled to −78° C., ammonia is bubbled through for 5 minutes and then a solution of 0.19 g of the compound obtained in the preceding step in 5 ml of THF is added and the mixture is left with stirring for 2 hours, allowing the temperature to rise to AT. The reaction mixture is concentrated under vacuum, the residue is taken up in water, the product obtained is triturated and the precipitate formed is filtered off with suction and washed with a propan-2-ol/PE mixture (50/50; v/v) and then with ether. This gives 0.08 g of the expected compound, m.p.=272-275° C.

$^1$H NMR: DMSO-$d_6$ (300 MHz): δ (ppm): 4.03: s: 3H; 4.21: s: 3H; 7.43-7.51: m: 2H; 7.67-7.70: m: 2H; 7.82-7.86: m: 1H; 8.26: s: 1H; 8.37: s: 1H; 12.90: se: 1H.

EXAMPLE 22

Compound 66

Ethyl 3-[3-(2,4-dichlorophenyl)-1,9-dimethyl-2-oxo-2,9-dihydro-1H-pyrido[2,3-b]indol-6-yl]-1,2,4-oxodiazole-5-carboxylate.

A solution of 0.17 g of the compound from Preparation 3.35 in 2 ml of 1,2-dichloroethane and 0.1 ml of pyridine is cooled to 0° C., 0.09 ml of ethyloxalyl chloride is added and the mixture is left with stirring for 30 minutes, allowing the temperature to rise to AT. It is subsequently heated at 80° C. for 2 hours. After cooling to AT, the precipitate formed is filtered off with suction. The precipitate is dissolved in DCM and MeOH and the solution is chromatographed on silica gel, eluting with an AcOEt/MeOH mixture (95/05; v/v). This gives 0.14 g of the expected compound.

The table below illustrates the chemical structures and the physical properties of some examples of compounds according to the invention. In this table Me represents methyl.

TABLE 3

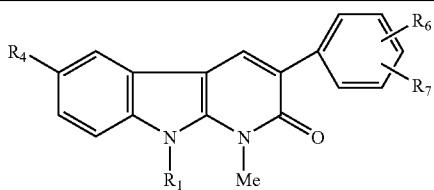

(I): R$_8$ = H
R$_5$ = H

| Compound | R$_1$ | R$_6$, R$_7$ | R$_4$ | Characterization |
|---|---|---|---|---|
| 1 | H | H | —CH=N—OH | m.p. = 255° C. |
| 2 | Me | 2,4-diCl | 5-methyl-3-methyl-1,2,4-oxadiazole | m.p. = 286° C. |
| 3 | H | 2,4-diCl | 5-methyl-3-methyl-1,2,4-oxadiazole | m.p. = 279° C. |
| 4 | Me | 2,4-diMe | 5-methyl-3-methyl-1,2,4-oxadiazole | NMR |
| 5 | Me | 2,4-diOMe | 5-methyl-3-methyl-1,2,4-oxadiazole | m.p. = 241° C. |
| 6 | H | 2,4-diMe | 5-methyl-3-methyl-1,2,4-oxadiazole | m.p. = 340° C. |
| 7 | H | 2,4-diOMe | —CH=N—OEt | m.p. = 295° C. |
| 8 | H | 2,4-diOMe | 5-methyl-3-phenyl-1,2,4-oxadiazole | NMR |
| 9 | Me | H | 5-methyl-3-methyl-1,2,4-oxadiazole | m.p. = 233° C. |
| 10 | Me | 2-Me, 5-F | 5-methyl-3-methyl-1,2,4-oxadiazole | m.p. = 280° C. |

TABLE 3-continued

[Structure: tricyclic scaffold with R4 on benzo ring, R1 on indole N, Me on pyridinone N, and 3-aryl substituent bearing R6, R7]

(I): R8 = H
R5 = H

| Compound | R1 | R6, R7 | R4 | Characterization |
|---|---|---|---|---|
| 11 | Me | 3-F, 4-Me | 5-methyl-3-methyl-1,2,4-oxadiazol-yl | m.p. = 273° C. |
| 12 | H | H | 5-methyl-3-methyl-1,2,4-oxadiazol-yl | NMR |
| 13 | H | 2,4-diCl | 5-methyl-3-amino-1,2,4-oxadiazol-yl | m.p. = 330° C. |
| 14 | Me | 2,4-diCl | 5-methyl-3-amino-1,2,4-oxadiazol-yl | m.p. = 293° C. |
| 15 | Me | 3-Me, 4-F | 5-methyl-3-methyl-1,2,4-oxadiazol-yl | m.p. = 130° C. |
| 16 | H | 3-Me, 4-F | 5-methyl-3-methyl-1,2,4-oxadiazol-yl | m.p. = 325° C. |
| 17 | H | 3-F, 4-Me | 5-methyl-3-methyl-1,2,4-oxadiazol-yl | m.p. = 320° C. |
| 18 | H | 2-Me, 5-F | 5-methyl-3-methyl-1,2,4-oxadiazol-yl | NMR |

TABLE 3-continued

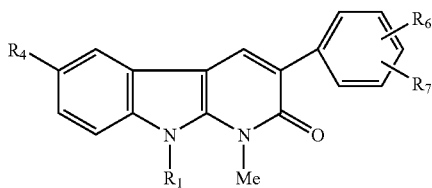

(I): R$_8$ = H
R$_5$ = H

| Compound | R$_1$ | R$_6$, R$_7$ | R$_4$ | Characterization |
|---|---|---|---|---|
| 19 | Me | 2,4-diCl | 5-methyl-3-phenyl-1,2,4-oxadiazole | m.p. = 319° C. |
| 20 | Me | 2,4-diCl | —CH=N—OH | m.p. = 287-290° C. |
| 21 | Me | 2,4-diCl | —CH=N—O—Et | |
| 22 | Me | 2,4-diCl | —CH=N—O—CH$_2$CH(CH$_3$)$_2$ | m.p. = 100-110° C. |
| 23 | Me | 2,4-diCl | —CH=N—O—CH$_2$—COOH | |
| 24 | Me | 2,4-diCl | —CH=N—O—CH$_2$—CO$_2$Et | m.p. = 160° C. |
| 25 | Me | 2,4-diCl | —CH=N—O—CH$_2$—CO—N(morpholine) | NMR |
| 26 | Me | 2,4-diOMe | 5-methyl-3-amino-1,2,4-oxadiazole | m.p. = 320-322° C. |
| 27 | Me | 2,4-diMe | 5-methyl-3-amino-1,2,4-oxadiazole | m.p. = 334° C. |
| 28 | Me | 2-Cl | 5-methyl-3-amino-1,2,4-oxadiazole | m.p. = 301° C. |
| 29 | Me | 4-Cl | 5-methyl-3-amino-1,2,4-oxadiazole | m.p. = 308-310° C. |
| 30 | Me | 3-Br | 5-methyl-3-amino-1,2,4-oxadiazole | m.p. = 290° C. |

TABLE 3-continued
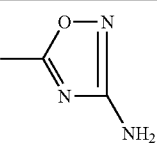
(I): R$_8$ = H
R$_5$ = H
| Compound | R$_1$ | R$_6$, R$_7$ | R$_4$ | Characterization |
|---|---|---|---|---|
| 31 | Me | 4-Br | 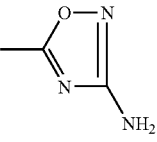 | NMR |
| 32 | Me | 3-F | 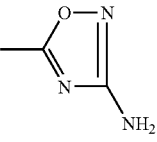 | m.p. = 309° C. |
| 33 | Me | 4-F | 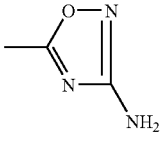 | mp. = 307-308° C. |
| 34 | Me | 3-Me | 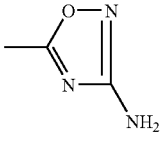 | m.p. = 295-296° C. |
| 35 | Me | 3-OMe | 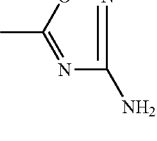 | m.p. = 274-278° C. |
| 36 | Me | 4-OMe | 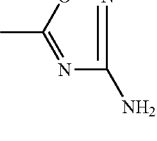 | m.p. = 182-185° C. |
| 37 | Me | 3-CN | 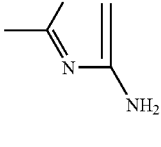 | m.p. 290-291° C. |
| 38 | Me | 4-CN | 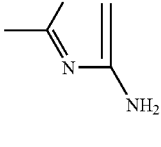 | NMR |

TABLE 3-continued (I): R₈ = H
R₅ = H

| Compound | R₁ | R₆, R₇ | R₄ | Characterization |
|---|---|---|---|---|
| 39 | Me | 4-CH₂NH₂ | 5-methyl-3-amino-1,2,4-oxadiazole | NMR |
| 40 | Me | 4-CH₂-morpholine | 5-methyl-3-amino-1,2,4-oxadiazole | NMR |
| 41 | Me | 2,4-diCl | 5-methyl-3-N(Me)₂-1,2,4-oxadiazole | m.p. = 320–324° C. |
| 42 | Me | 2,4-diCl | 5-methyl-3-NHCO-cyclopropyl-1,2,4-oxadiazole | m.p. = 292–295° C. |
| 43 | Me | 2,4-diCl | 5-methyl-3-NHCOCH₂N(Me)₂-1,2,4-oxadiazole | m.p. = 260° C. |
| 44 | Me | 2,4-diCl | 5-methyl-3-NH—SO₂—Me-1,2,4-oxadiazole | m.p. = 263–266° C. |
| 45 | Me | 3-F | 5-methyl-3-Me-1,2,4-oxadiazole | NMR |
| 46 | Me | 4-OCH₂-morpholine | 5-methyl-3-Me-1,2,4-oxadiazole | NMR |

TABLE 3-continued (I): R$_8$ = H
R$_5$ = H

| Compound | R$_1$ | R$_6$, R$_7$ | R$_4$ | Characterization |
|---|---|---|---|---|
| 47 | Et | 2,4-diCl | 3-Me-1,2,4-oxadiazol-5-yl (5-Me, 3-Me oxadiazole) | NMR |
| 48 | Me | 3,5-diF | 3-Me-1,2,4-oxadiazol-5-yl | NMR |
| 49 | —CH$_2$CN | 2,4-diCl | 3-Me-1,2,4-oxadiazol-5-yl | |
| 50 | —CH$_2$CH$_2$—N(morpholino) | 2,4-diCl | 3-Me-1,2,4-oxadiazol-5-yl | |
| 51 | Me | 2,4-diCl | 5-Me-1,2,4-oxadiazol-3-yl-CH$_2$—O—phenyl | NMR |
| 52 | Me | 2-OMe | 5-Me-3-NH$_2$-1,2,4-oxadiazole | m.p. = 271-272° C. |
| 53 | Me | 2,4-diCl | —C(Me)=N—OH | |
| 54 | Me | 2,4-diCl | —C(Me)=N—O—Et | NMR |
| 55 | Me | H | 5-Me-2-NH$_2$-1,3,4-oxadiazole | m.p. = 308-309° C. |

TABLE 3-continued (I): R$_8$ = H
R$_5$ = H

| Compound | R$_1$ | R$_6$, R$_7$ | R$_4$ | Characterization |
|---|---|---|---|---|
| 56 | Me | 2,4-diCl | 2-amino-5-methyl-1,3,4-oxadiazole | m.p. = 304–305° C. |
| 57 | H | 2,4-diOMe | 2-amino-5-methyl-1,3,4-oxadiazole | NMR |
| 58 | Me | 2,4-diCl | 2,5-dimethyl-1,3,4-oxadiazole | m.p. = 311–316° C. |
| 59 | Me | 2,4-diCl | 3,5-dimethyl-1,2,4-oxadiazole | m.p. = 306–307° C. |
| 60 | Me | 2,4-diCl | 5-amino-3-methyl-1,2,4-oxadiazole | m.p. = 272–275° C. dec |
| 61 | Me | 2,4-diCl | 5-dimethylamino-3-methyl-1,2,4-oxadiazole | m.p. = 287–289° C. |
| 62 | Me | 2,4-diCl | 5-(cyclopropylmethylamino)-3-methyl-1,2,4-oxadiazole | m.p. = 279–283° C. |
| 63 | Me | 2,4-diCl | 5-(3-morpholinopropylamino)-3-methyl-1,2,4-oxadiazole | m.p. = 228–230° C. |

TABLE 3-continued (I): $R_8 = H$
$R_5 = H$

| Compound | $R_1$ | $R_6, R_7$ | $R_4$ | Characterization |
|---|---|---|---|---|
| 64 | Me | 2,4-diCl | (3-methyl-1,2,4-oxadiazol-5-yl)-NH-cyclopropyl | m.p. = 272-276° C. |
| 65 SSR 19557 | Me | 2,4-diCl | (3-methyl-1,2,4-oxadiazol-5-yl)-NH(CH$_2$)$_2$N(Me)$_2$ | m.p. = 145-150° C. |
| 66 | Me | 2,4-diCl | (3-methyl-1,2,4-oxadiazol-5-yl)-C(O)-O-Et | NMR |
| 67 | Me | 3-Cl | (5-methyl-1,3,4-oxadiazol-2-yl)-NH$_2$ | NMR |

$^1$H NMR: DMSO-d$_6$ (300 MHz): Compound 4: δ(ppm): 2.15: s: 3H; 2.32: s: 3H; 2.41 s: 3H; 4.02: s: 3H; 4.22: s 3H; 7.01-7.1: m: 3H; 7.82: d: 1H; 7.96: dd: 1H; 8.28: s: 1H; 8.68: s: 1H.
$^1$H NMR: DMSO-d$_6$ (300 MHz): Compound 8: δ(ppm): 3.69: s: 3H; 3.72: s: 3H; 3.81: s: 3H; 6.55-6.59: dd: 1H; 6.63: d: 1H; 7.18: d: 1H; 7.55-7.62: m: 3H; 7.68: d: 1H; 8.01-8.05: dd: 1H; 8.10-8.16: m: 2H; 8.25: s: 1H; 8.73: d: 1H; 12.48: s: 1H.
$^1$H NMR: DMSO-d$_6$ (300 MHz): Compound 12: δ(ppm): 2.48: s: 3H; 3.79: s: 3H; 7.37: d: 1H; 7.44-7.49: m: 2H; 7.69: d: 1H; 7.72-7.84: m: 2H; 7.99: d: 1H; 8.67: s: 1H; 8.81: s: 1H; 12.6: se: 1H.
$^1$H NMR: DMSO-d$_6$ (300 MHz): Compound 18: δ(ppm): 2.17: s: 3H; 2.40: s: 3H; 3.71: s: 3H; 7-7.25: m: 2H; 7.6: d: 1H; 7.25: d: 1H; 7.9: d: 1H; 8.75: s: 1H; 8.65: s: 1H.
$^1$H NMR: DMSO-d$_6$ (300 MHz): Compound 25: δ(ppm): 3.44: se: 4H; 3.56: se: 4H; 4.01: s: 3H; 4.17: s: 3H; 4.84: s: 2H; 7.42-7.49: m: 2H; 7.55: dd: 1H; 7.66-7.69: m: 2H; 8.10: d: 1H; 8.26: s: 1H; 8.38: s: 1H.
$^1$H NMR: DMSO-d$_6$ (200 MHz): Compound 31: δ(ppm):; 4.0: s: 3H; 4.2: s: 3H; 6.3: s: 2H; 7.5: d: 2H; 7.7-8.0: m: 4H; 8.65: d: 2H.
$^1$H NMR: DMSO-d$_6$ (300 MHz): Compound 32: δ(ppm): 4.04: s: 3H; 4.20: s: 3H; 6.33: s: 2H; 7.12: t: 1H; 7.44: q: 1H; 7.70: m: 2H; 7.80: d: 1H; 7.90: d: 1H; 8.69: s: 1H; 8.77: s: 1H.
$^1$H NMR: DMSO-d$_6$ (200 MHz): Compound 38: δ(ppm):; 4.05: s: 3H; 4.15: s: 3H; 6.3: s: 2H; 7.4: d: 2H; 7.75-8.0: m: 4H; 8.6: d: 2H.
$^1$H NMR: DMSO-d$_6$/TFA (200 MHz): Compound 40: δ(ppm):; 3.95: s: 2H; 3.55-3.7: m: 8H; 4.1: s: 3H; 4.2: s: 3H; 7.55: d: 2H; 7.8-7.95: m: 4H; 8.6: d: 2H.
$^1$H NMR: DMSO-d$_6$ (300 MHz): Compound 43: δ(ppm): 2.30: s: 6H; 3.23: s: 2H; 4.05: s: 3H; 4.25: s: 3H; 7.47-7.50: m: 2H; 7.72: s: 1H; 7.89: d: 1H; 7.99: d: 1H; 8.39: s: 1H; 8.70: s: 1H; 10.90: s: 1H.
$^1$H NMR: DMSO-d$_6$ (300 MHz): Compound 45: δ(ppm): 2.42: s: 3H; 4.04: s: 3H; 4.21: s: 3H; 7.09-7.15: m: 1H; 7.41-7.48: q: 1H; 7.71-7.75: m: 2H; 7.83: d: 1H; 7.97-8.00: dd: 1H; 8.06: s: 2H.
$^1$H NMR: MeOD-d$_4$ (300 MHz): Compound 46: δ(ppm): 2.43: s: 3H; 2.63: t: 4H; 2.84: t: 2H; 3.74: t: 4H; 4.07: s: 3H; 4.19: t: 5H; 7.00: d 2H; 7.63: d: 3H; 8.00: d: 1H; 8.22: s: 1H; 8.47: s: 1H.
$^1$H NMR: DMSO-d$_6$ (300 MHz): Compound 47: δ(ppm): 1.47: t: 3H; 2.42: s: 3H; 3.99: s: 3H; 4.72: q: 2H; 7.43-7.51: m: 2H; 7.69: d: 1H; 7.86: d: 1H; 8.01: d: 1H; 8.40: s: 1H; 8.71: s: 1H.
$^1$H NMR: DMSO-d$_6$ (300 MHz): Compound 48: δ(ppm): 2.42: s: 3H; 4.03: s: 3H; 4.20: s: 3H; 7.09-7.16: m: 1H; 7.67-7.72: m: 2H; 7.82: d: 1H; 7.97-8.00: dd: 1H; 8.81: s: 1H; 8.92: s: 1H.
$^1$H NMR: DMSO-d$_6$ (300 MHz): Compound 51: δ(ppm): 4.04: s: 3H; 4.24: s: 3H; 5.35: s: 2H; 7.01: t: 1H; 7.09: d: 2H; 7.34: t: 2H; 7.43-7.52: m: 2H; 7.70: s: 1H; 7.87: d: 1H; 8.03: dd: 1H; 8.49: s: 1H; 8.77: s: 1H.
$^1$H NMR: DMSO-d$_6$ (300 MHz): Compound 54: δ(ppm): 1.28: t: 3H; 2.26: s: 3H; 4.02: s: 3H; 4.15-4.22: m: 5H; 7.42-7.47: m: 2H; 7.60-7.70: m: 3H; 8.20: s: 1H; 8.32: s: 1H.
$^1$H NMR: DMSO-d$_6$ (300 MHz): Compound 57: δ(ppm): 3.67: s: 3H; 3.71: s: 3H; 3.80: s: 3H; 6.54-6.57: dd: 1H; 6.62: d: 1H; 7.09: s: 2H; 7.17: d: 1H; 7.58: d: 1H; 7.65-7.69: dd: 1H; 8.12: s: 1H; 8.21: s: 1H; 12.24: s: 1H.
$^1$H NMR: DMSO-d$_6$ (300 MHz): Compound 66: δ(ppm): 1.37: t: 3H; 4.02: s: 3H; 4.21: s: 3H; 4.47: q: 2H; 7.44-7.47: m: 2H; 7.69: d: 1H; 7.82: d:. 1H; 7.96: dd: 1H; 8.48: s: 1H; 8.64: s: 1H.
$^1$H NMR: DMSO-d$_6$ (300 MHz): Compound 67: δ(ppm): 4.0: s: 3H; 4.2: s: 3H; 6.33: s: 2H; 7.45-7.9: m: 6H; 8.6: s: 1H; 8.7: s: 1H.

The compounds of formula (I) according to the present invention were tested in vitro on a human breast cancer cell line: the MDA-MB-231 line available from the American Type Culture Collection (reference HTB26).

The antiproliferative effect is evaluated according to J. M. Derocq et al., FEBS Letters, 1998, 425, 419-25: the level of incorporation of [$^3$H]thymidine in the DNA of the treated cells is measured after incubating a compound of formula (I)

for 96 hours. The inhibitory concentration 50 ($IC_{50}$) is defined as the concentration which inhibits cell proliferation by 50%.

The compounds according to the invention exhibit an $IC_{50}$ generally of less than 10 μM with regard to the MDA-MB-231 line.

The compounds of formula (I) were also tested on another human breast cancer cell line, a "multi-drug-resistant" (MDR) line referred to as MDA-$A_1$. This line is described by E. Collomb, C. Dussert and P.M. Martin in Cytometry, 1991, 12(1), 15-25.

The term "multi-resistant" which describes this line means that the said line is generally not very sensitive to the chemotherapeutic drugs commonly used and in particular to antimitotics of natural origin, such as paclitaxel, vincristine or vinblastine.

The compounds according to the invention exhibit an $IC_{50}$ generally of less than 10 μM with regard to the multi-resistant MDA-$A_1$ line.

Thus, according to the present invention, it is apparent that the compounds of formula (I) inhibit the proliferation of tumour cells, including that of cells exhibiting multi-resistance. It is thus apparent that the compounds according to the invention have an anti-cancer activity.

Thus, according to another of its aspects, the invention provides medicinal products which comprise a compound of formula (I) or an addition salt of the latter with a pharmaceutically acceptable acid or else a hydrate or a solvate of the compound of formula (I).

These medicinal products find their use in therapeutics, in particular in the treatment or prevention of diseases caused or exacerbated by the proliferation of tumour cells.

These compounds, as inhibitors of the proliferation of tumour cells, are of use in the treatment of all types of neoplasms, of any origin, whether solid or not, benign or malignant, primary or metastatic, carcinomas, sarcomas, adenomas or adenocarcinomas, in particular: breast cancer; lung cancer; cancer of the small intestine, cancer of the colon and of the rectum; cancer of the respiratory tract, of the oropharynx and of the hypopharynx; cancer of the oesophagus; liver cancer, stomach cancer, cancer of the bile ducts, cancer of the gall bladder, cancer of the pancreas; cancers of the urinary tract, including kidney, urothelium and bladder; cancers of the female genital tract, including cancer of the uterus, cervix and ovaries, choriocarcinoma and trophoblastoma; cancers of the male genital tract, including cancer of the prostate, seminal vesicles and testicles, tumours of the germinal cells; cancers of the endocrine glands, including cancer of the thyroid, pituitary gland and adrenal glands; skin cancers, including haemangiomas, melanomas and sarcomas, including Kaposi's sarcoma; tumours of the brain, nerves, eyes and meninges, including astrocytomas, gliomas, glioblastomas, retinoblastomas, neurinomas, neuroblastomas, schwannomas and meningiomas; tumours resulting from haematopoietic malignant tumours, including leukaemias, chloromas, plasmacytomas, fungoid mycosis, T-cell lymphoma or leukaemia, non-Hodgkin's lymphoma, malignant haemopathies and myelomas.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or solvate of the said compound, and at least one pharmaceutically acceptable excipient.

The said excipients are selected, according to the pharmaceutical form and the method of administration desired, from the usual excipients which are known to the skilled person.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, solvate or hydrate where appropriate, can be administered in unit administration form, as a mixture with conventional pharmaceutical excipients, to animals and human beings for the prophylaxis or treatment of the above disorders or diseases.

The appropriate unit administration forms comprise forms by the oral route, such as tablets, soft or hard gelatin capsules, powders, granules and oral solutions or suspensions, sublingual, buccal, intratracheal, intraocular or intranasal, by inhalation, administration forms, topical, transdermal, subcutaneous, intramuscular or intravenous administration forms, rectal administration forms and implants. Use may be made, for topical application, of the compounds according to the invention in creams, gels, ointments or lotions.

The compounds of formula (I) above can be used at daily doses of 0.002 to 2000 mg per kilogram of body weight of the mammal to be treated, preferably at daily doses of 0.1 to 300 mg/kg. In humans, the dose can vary preferably from 0.02 to 10 000 mg per day, more particularly from 1 to 3000 mg, depending on the age of the subject to be treated or the type of treatment: prophylactic or curative.

There may be specific cases where higher or lower dosages are appropriate; such dosages do not depart from the scope of the invention. According to usual practice, the dosage appropriate to each patient is determined by the doctor according to the method of administration and the weight and response of the said patient.

The present invention, according to another of its aspects, also relates to a method of treating the pathologies indicated above which comprises the administration, to a patient, of an effective dose of a compound according to the invention, or one of its pharmaceutically acceptable salts or hydrates or solvates.

According to the present invention, the compound or compounds of formula (I) can be administered in combination with one (or more) anti-cancer active principle(s), in particular anti-tumour compounds, such as alkylating agents, such as alkylsulphonates (busulfan), dacarbazine, procarbazine, nitrogen mustards (chlormethine, melphalan, chlorambucil), cyclophosphamide or ifosfamide; nitrosoureas, such as carmustine, lomustine, semustine or streptozocin; anti-neoplastic alkaloids, such as vincristine or vinblastine; taxanes, such as paclitaxel or taxotere; anti-neoplastic antibiotics, such as acti-nomycin; intercalating agents, anti-neoplastic anti-metabolites, folate antagonists or methotrexate; purine synthesis inhibitors; purine analogues, such as mercaptopurine or 6-thioguanine; pyrimidine synthesis inhibitors, aromatase inhibitors, capecitabine or pyrimidine analogues, such as fluorouracil, gemcitabine, cytarabine and cytosine arabinoside; brequinar; topoisomerase inhibitors, such as camptothecin or etoposide; anticancer hormonal agonists and antagonists, including tamoxifen; kinase inhibitors, imatinib; growth factor inhibitors; antiinflammatories, such as pentosan polysulphate, corticosteroids, prednisone, dexamethasone or anthracyclines, including doxorubicin, bleomycin, mitomycin and mithramycin; anti-cancer metal complexes, platinum complexes, cisplatin, carboplatin or oxaliplatin; interferon-alpha, triphenyl thiophosphoramide or altretamine; antiangiogenic agents, such as bevacizumab; proteasome inhibitors, such as bortezomib; thalidomide; immunotherapy adjuvants; or vaccines.

The present invention, according to another of its aspects, likewise relates to a method of treating the pathologies indicated above which comprises the administration, to a patient, of an effective dose of a compound according to the invention or one of its pharmaceutically acceptable salts or hydrates or solvates.

What is claimed is:

1. A compound of formula:

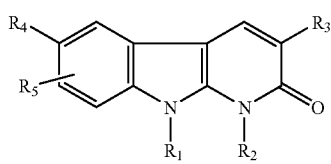

(I)

wherein
R$_1$ represents a hydrogen atom; a (C$_1$-C$_4$)alkyl group; a group —(CH$_2$)$_m$OH; a group —(CH$_2$)$_m$CN; or a group —(CH$_2$)$_m$NR$_9$R$_{10}$;
R$_2$ represents a hydrogen atom or a (C$_1$-C$_4$)alkyl group;
R$_3$ represents a phenyl substituted by R$_6$, R$_7$, R$_8$;
R$_4$ represents
a heterocyclic radical selected from

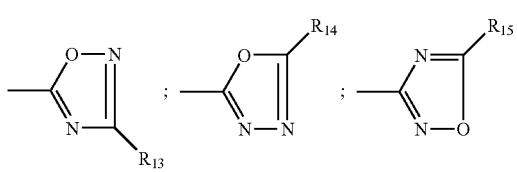

R$_5$ represents a hydrogen atom or a (C$_1$-C$_4$)alkyl group;
R$_6$, R$_7$ and R$_8$ represent, each independently of one another, a hydrogen atom; a halogen atom; a (C$_1$-C$_4$) alkyl group; a (C$_1$-C$_4$)alkoxy group; a hydroxyl; a cyano; a group —(CH$_2$)$_n$NR$_9$R$_{10}$; or a group —O—(CH$_2$)$_m$NR$_9$R$_{10}$;
R$_9$ and R$_{10}$ represent, each independently of one another, a hydrogen atom or a (C$_1$-C$_4$)alkyl group;
or else R$_9$ and R$_{10}$, together with the nitrogen atom to which they are bonded, constitute a heterocyclic radical selected from pyrrolidin-1-yl, piperidin-1-yl, morpholin-4-yl or piperazin-1-yl unsubstituted or substituted in position 4 by a (C$_1$-C$_4$)alkyl;
R$_{13}$ represents a hydrogen atom; a (C$_1$-C$_4$)alkyl group; a phenyl; a group —NR$_{17}$R$_{18}$; or a

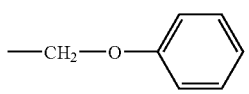

group;
R$_{14}$ represents a hydrogen atom; a (C$_1$-C$_4$)alkyl group; or a group —NR$_{17}$R$_{18}$;
R$_{15}$ represents a hydrogen atom; a (C$_1$-C$_4$)alkyl group; a group —NR$_{19}$R$_{20}$; or a —COO(C$_1$-C$_4$)alkyl group;
R$_{17}$ and R$_{18}$ represent, each independently, a hydrogen atom or a (C$_1$-C$_4$)alkyl group; R$_{18}$ may also represent a group —COR$_{21}$; or a group —SO$_2$R$_{22}$;

R$_{19}$ and R$_{20}$ represent, each independently, a hydrogen atom or a (C$_1$-C$_4$)alkyl group; R$_{20}$ may also represent a (C$_3$-C$_6$)cycloalkyl group, a (C$_3$-C$_6$)cycloalkylmethyl group or a group —(CH$_2$)$_m$NR$_9$R$_{10}$;
R$_{21}$ represents a (C$_1$-C$_4$)alkyl group; a (C$_3$-C$_6$)cycloalkyl group; or a group —(CH$_2$)$_m$NR$_9$R$_{10}$;
R$_{22}$ represents a (C$_1$-C$_4$)alkyl group;
m is 1, 2 or 3; and
n is 0, 1, 2 or 3;
or a pharmaceutically acceptable salt of said compound.

2. A compound according to claim 1, wherein
R$_1$ represents a hydrogen atom, a methyl, an ethyl, a cyanomethyl or a 2-morpholin-4-ylethyl;
R$_2$ represents a methyl;
R$_3$ represents a phenyl, a 3-bromophenyl, a 4-bromophenyl, a 2-chlorophenyl, a 3-chlorophenyl, a 4-chlorophenyl, a 3-fluorophenyl, a 4-fluorophenyl, a 3-methylphenyl, a 2-methoxyphenyl, a 3-methoxyphenyl, a 4-methoxyphenyl, a 3-cyanophenyl, a 4-cyanophenyl, a 2,4-dichlorophenyl, a 3,5-difluorophenyl, a 2,4-dimethylphenyl, a 2,4-dimethoxyphenyl, a 2-methyl-5-fluorophenyl, a 3-fluoro-4-methylphenyl, a 3-methyl-4-fluorophenyl, a 4-(aminomethyl)phenyl, a 4-(morpholin-4-ylmethyl)phenyl or a 4-(2-morpholin-4-ylethoxy)phenyl;
R$_4$ represents:
a 3-methyl-1,2,4-oxadiazol-5-yl, a 3-phenyl-1,2,4-oxadiazol-5-yl, a 3-amino-1,2,4-oxadiazol-5-yl, a 3-(dimethylamino)-1,2,4-oxadiazol-5-yl, a 3-[(cyclopropylcarbonyl)amino]-1,2,4-oxadiazol-5-yl, a 3-[(N,N-dimethylglycyl)amino]-1,2,4-oxadiazol-5-yl, a 3[(methylsulphonyl)amino]-1,2,4-oxadiazol-5-yl or a 3-(phenoxymethyl)-1,2,4-oxadiazol-5-yl;
a 5-methyl-1,3,4-oxadiazol-2-yl or a 5-amino-1,3,4-oxadiazol-2-yl; or
a 5-methyl-1,2,4-oxadiazol-3-yl, a 5-amino-1,2,4-oxadiazol-3-yl, a 5-(dimethylamino)-1,2,4-oxadiazol-3-yl, a 5-(cyclopropylamino)-1,2,4-oxadiazol-3-yl, a 5-[(cyclopropylmethyl)amino]-1,2,4-oxadiazol-3-yl, a 5-[(3-morpholin-4-ylpropyl)amino]-1,2,4-oxadiazol-3-yl, a 5-[[2-(dimethylamino)ethyl]amino]-1,2,4-oxadiazol-3-yl or a 5-(ethoxycarbonyl)-1,2,4-oxadiazol-3-yl;
R$_5$ represents a hydrogen atom;
or a pharmaceutically acceptable salt of said compound.

3. A compound of formula (I), according to claim 1, selected from the group consisting of:
6-(3-amino-1,2,4-oxadiazol-5-yl)-3-(2,4-dichlorophenyl)-1,9-dimethyl-1,9-dihydro-2H-pyrido[2,3-b]indol-2-one;
5-[3-(4-chlorophenyl)-1,9-dimethyl-2,9-dihydro-1H-pyrido[2,3-b]indol-6-yl]-1,2,4-oxadiazol-3-amine;
5-[3-(3-fluorophenyl)-1,9-dimethyl-2,9-dihydro-1H-pyrido[2,3-b]indol-6-yl]-1,2,4-oxadiazol-3-amine;
5-[1,9-dimethyl-3-(3-methylphenyl)-2,9-dihydro-1H-pyrido[2,3-b]indol-6-yl]-1,2,4-oxadiazol-3-amine;
3-[4-(aminomethyl)phenyl]-6-(3-amino-1,2,4-oxadiazol-5-yl)-1,9-dimethyl-1,9-dihydro-2H-pyrido[2,3-b]indol-2-one;
5-[1,9-dimethyl-3-[4-morpholin-4-ylmethyl)phenyl]-2,9-dihydro-1H-pyrido[2,3-b]indol-6-yl]-1,2,4-oxadiazol-3-amine;
5-[3-(2,4-dichlorophenyl)-1,9-dimethyl-2,9-dihydro-1H-pyrido[2,3-b]indol-6-yl]-1,3,4-oxadiazol-2-amine; and
N'-[3-[3-(2,4-dichlorophenyl)-1,9-dimethyl-2,9-dihydro-1H-pyrido[2,3-b]indol-6-yl]-1,2,4-oxadiazol-5-yl]-N,N-dimethylethane-1,2-diamine;
or a pharmaceutically acceptable salt of said compound.

4. A process for preparing a compound of formula (I) according to claim 1 in which $R_4 =$ 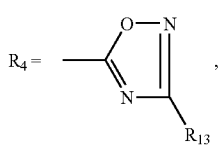, wherein
a compound of formula

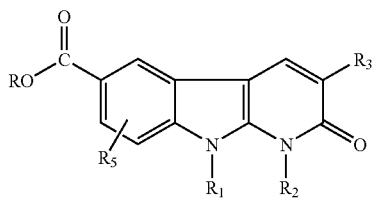 (IV)

in which $R_1$, $R_2$, $R_3$ and $R_5$ are as defined for a compound of formula (I) in claim 1 and R represents a hydrogen atom or a $(C_1\text{-}C_4)$alkyl group is reacted with an oxime derivative of formula

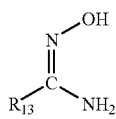 (V)

in which $R_{13}$ is as defined for a compound of formula (I) in claim 1.

5. A process for preparing a compound of formula (I) according to claim 1 in which $R_4 =$ 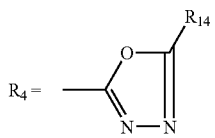, wherein
a compound of formula

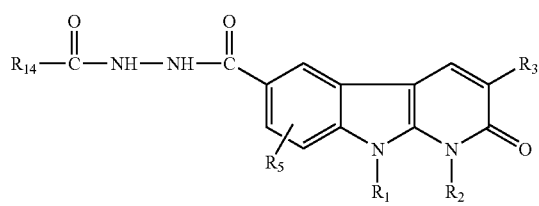 (IX)

in which $R_1$, $R_2$, $R_3$, $R_5$ and $R_{14}$ are as defined for a compound of formula (I) in claim 1 is cyclized.

6. A process for preparing a compound of formula (I) according to claim 1 in which $R_4 =$ 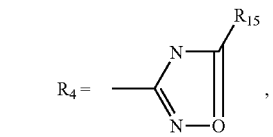, wherein
a compound of formula

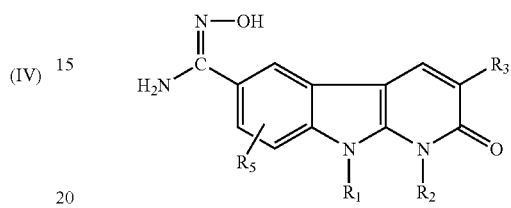 (XI)

in which $R_1$, $R_2$, $R_3$ and $R_5$ are as defined for a compound of formula (I) in claim 1 is reacted with:
a) trichloroacetyl chloride, in the presence of a base, to give a compound of formula

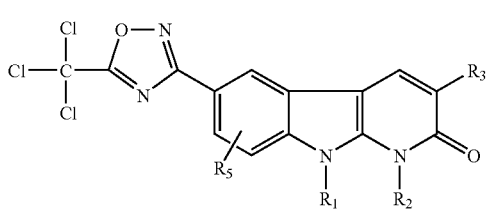 (XII)

and the compound of formula (XII) thus obtained is reacted with an amine of formula $HNR_{19}R_{20}$, when the preparation is required of a compound of formula (I) in which $R_{15}=NR_{19}R_{20}$; or
b) an anhydride of formula $(R_{15}CO)_2O$, when the preparation is required of a compound of formula (I) in which $R_{15}=(C_1\text{-}C_4)$alkyl; or
c) a derivative of oxalic acid of formula

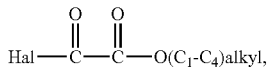

in which Hal represents a halogen atom, when the preparation is required of a compound of formula (I) in which $R_{15}=COO(C_1\text{-}C_4)$alkyl.

7. A pharmaceutical composition comprising a compound of formula (I) according to claim 1, or a pharmaceutically acceptable salt of said compound; and at least one pharmaceutically acceptable excipient.

8. A pharmaceutical composition comprising a compound of formula (I) according to claim 2, or a pharmaceutically acceptable salt of said compound; and at least one pharmaceutically acceptable excipient.

9. A pharmaceutical composition comprising a compound of formula (I) according to claim 3, or a pharmaceutically acceptable salt of said compound; and at least one pharmaceutically acceptable excipient.

* * * * *

UNITED STATES PATENT AND TRADEMARK OFFICE
CERTIFICATE OF CORRECTION

| | |
|---|---|
| PATENT NO. | : 7,812,165 B2 |
| APPLICATION NO. | : 11/582769 |
| DATED | : October 12, 2010 |
| INVENTOR(S) | : Bernard Bourrie et al. |

It is certified that error appears in the above-identified patent and that said Letters Patent is hereby corrected as shown below:

Title page, item (56), in column 2, under "Other Publications", line 4, delete "Grandular" and insert -- Glandular --, therefor.

Title page, item (56), in column 2, under "Other Publications", line 9, delete "station," and insert -- edition, --, therefor.

In column 4, line 48, before "3-methyl" insert -- a --.

In column 10, line 22, delete "$R_2 = H$," and insert -- $R_2 \neq H$, --, therefor.

In column 11, line 38-39, delete "N,N-dimethyl-formamide" and insert -- N,N-dimethylformamide --, therefor.

In column 11, line 47, delete "0C" and insert -- 0° C --, therefor.

In column 11, line 58, delete "$R_1H$" and insert -- $R_1=H$ --, therefor.

In column 14, line 27, delete "$R == H$" and insert -- $R=H$ --, therefor.

In column 14, line 60, delete "$R'_4 == CN$)" and insert -- $R'_4=CN$) --, therefor.

In column 22, in Table 1, Preparations 2.19, line 46, delete "(300 MHz)" and insert -- (300 MHz): --, therefor.

In column 22, line 55, delete "phenyllacrylate." and insert -- phenyl]acrylate. --, therefor.

In column 23, line 37, delete "CUCN" and insert -- CuCN --, therefor.

Signed and Sealed this
Thirty-first Day of May, 2011

David J. Kappos
*Director of the United States Patent and Trademark Office*

In column 23, line 63, delete "8.13 ppm: S:" and insert -- 8.13 ppm: s: --, therefor.

In column 23, line 64, delete "8.43 ppm: S:" and insert -- 8.43 ppm: s: --, therefor.

In column 23, line 64, delete "10.00 ppm: S:" and insert -- 10.00 ppm: s: --, therefor.

In column 32, line 54, delete "(300 MHz)" and insert -- (300 MHz): --, therefor.

In column 35, line 19, delete "1H" and insert -- $^{1}$H --, therefor.

In column 38, line 62, delete "amino)" and insert -- amino] --, therefor.

In column 39, line 58, delete "haemopathies" and insert -- hemopathies --, therefor.

In column 64, line 39, in claim 6, delete "$R_{15}$≡" and insert -- $R_{15}$= --, therefor.

In column 64, line 42, in claim 6, delete "$R_{15}$≡" and insert -- $R_{15}$= --, therefor.

In column 64, line 50, in claim 6, delete "$R_{15}$≡" and insert -- $R_{15}$= --, therefor.